US012703736B2

(12) United States Patent
Wei et al.

(10) Patent No.: US 12,703,736 B2
(45) Date of Patent: Aug. 11, 2026

(54) FUSION PEPTIDE FOR TREATING AUTOIMMUNE DISEASE

(71) Applicant: BEIJING ZEQIN BIOMEDICAL CO., LTD, Beijing (CN)

(72) Inventors: Huawei Wei, Beijing (CN); Chenggang Yang, Beijing (CN)

(73) Assignee: BEIJING ZEQIN BIOMEDICAL CO., LTD, Beijing (CN)

( * ) Notice: Subject to any disclaimer, the term of this patent is extended or adjusted under 35 U.S.C. 154(b) by 812 days.

(21) Appl. No.: 17/996,451

(22) PCT Filed: Apr. 18, 2020

(86) PCT No.: PCT/CN2020/085447
§ 371 (c)(1),
(2) Date: Oct. 18, 2022

(87) PCT Pub. No.: WO2021/208106
PCT Pub. Date: Oct. 21, 2021

(65) Prior Publication Data

US 2023/0227533 A1 Jul. 20, 2023

(51) Int. Cl.

| | |
|---|---|
| ***C07K 14/705*** | (2006.01) |
| ***A61P 37/00*** | (2006.01) |
| ***C07K 14/195*** | (2006.01) |
| ***C07K 19/00*** | (2006.01) |

(52) U.S. Cl.
CPC ........ *C07K 14/70596* (2013.01); *A61P 37/00* (2018.01); *C07K 14/195* (2013.01); *C07K 19/00* (2013.01); *C07K 2319/03* (2013.01)

(58) Field of Classification Search
CPC ....................... C07K 14/70596; C07K 14/195; C07K 19/00; C07K 2319/03; C07K 14/70521; A61P 37/00
See application file for complete search history.

(56) References Cited

U.S. PATENT DOCUMENTS 9,669,078 B2 * 6/2017 Andersen ................ A61P 31/12
2018/0362591 A1 * 12/2018 Pedersen ................ A61K 39/12

FOREIGN PATENT DOCUMENTS

| | | | | |
|---|---|---|---|---|
| CN | 103917243 A | | 7/2014 | |
| CN | 109467607 A | | 3/2019 | |
| CN | 109517045 A | * | 3/2019 | ......... A61K 49/0056 |
| CN | 109517073 A | * | 3/2019 | ............. A61K 47/64 |
| CN | 110713522 A | | 1/2020 | |
| CN | 110760008 A | | 2/2020 | |
| CN | 110790829 A | | 2/2020 | |
| WO | 2017220602 A1 | | 12/2017 | |

OTHER PUBLICATIONS

Espacenet Patent Translate: machine-generated translation of the Description of CN109517073A, originally published Mar. 26, 2019. (24 pages total) (Year: 2019).*
Wei et al. 2017. "pH-responsive pHLIP (pH low insertion peptide) nanoclusters of superparamagnetic iron oxide nanoparticles as a tumor-selective MRI contrast agent". Acta biomaterialia, 55, 194-203, on the IDS filed Oct. 18, 2022 (Year: 2017).*
English Language Translation of CN-109517045-A, including description and claims sections (79 pages total). Originally published on Mar. 26, 2019. Accessed Sep. 6, 2025 from ESPACENET <worldwide.espacenet.com/publicationDetails/biblio?CC=CN&NR=109517045A&KC=A&FT=D>. (Year: 2019).*
Sun et al. 2021. "pH Low Insertion Peptide-Modified Programmed Cell Death-Ligand 1 Potently Suppresses T-Cell Activation Under Acidic Condition". Front. Immunol. 12:794226. doi: 10.3389/fimmu.2021.794226 (Year: 2021).*
Jia, Xue-Li et al.; "Research situation of pH low insertion peptides"; Acta Pharmaceutica Sinica; vol. 53, No. 3, Dec. 31, 2018, pp. 375-382.
Wei, Yushuang et al.; "pH-responsive pHLIP (pH low insertion peptide) nanoclusters of superparamagnetic iron oxide nanoparticles as a tumor-selective MRI contrast agent", Acta Biomaterialia; vol. 55, Mar. 29, 2017; pp. 194-203.

* cited by examiner

*Primary Examiner* — Anand U Desai
*Assistant Examiner* — Andrew T Moehlman
(74) *Attorney, Agent, or Firm* — NKL Law; Allen Xue

(57) ABSTRACT

PDL1-pHLIP, a preparation method of the PDL1-pHLIP, and an application of the PDL1-pHLIP in treatment of autoimmune diseases are provided. A fusion peptide is prepared by binding a pH low insertion peptide and an extracellular domain of PDL1. The pH low insertion peptide may be inserted onto a cell membrane of a focus tissue in an acid environment; the PDL1 bound to the pH low insertion peptide is subjected to targeting localization at the focus by utilizing the above properties of the pH low insertion peptide; a PD-1/PD-L1 negative signal of the focus tissue is enhanced by utilizing the pH low insertion peptide; and immune response of effector T cells is suppressed at the source, thereby achieving an effect of preventing and treating the autoimmune diseases.

8 Claims, 14 Drawing Sheets

Specification includes a Sequence Listing.

SEQUENCE LISTING

```
<160> NUMBER OF SEQ ID NOS: 30

<210> SEQ ID NO 1
<211> LENGTH: 36
<212> TYPE: PRT
<213> ORGANISM: Artificial Sequence
<220> FEATURE:
<223> OTHER INFORMATION: the Wild-type of the pH low insertion peptide

<400> SEQUENCE: 1
```

-continued

```
Ala Cys Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asp Ala
            20                  25                  30

Asp Glu Gly Thr
        35


<210> SEQ ID NO 2
<211> LENGTH: 32
<212> TYPE: PRT
<213> ORGANISM: Artificial Sequence
<220> FEATURE:
<223> OTHER INFORMATION: the variant 1 of the Wild-type of the pH low
      insertion peptide

<400> SEQUENCE: 2

Ala Cys Glu Asp Gln Asn Pro Tyr Trp Ala Arg Tyr Ala Asp Trp Leu
1               5                   10                  15

Phe Thr Thr Pro Leu Leu Leu Leu Asp Leu Ala Leu Leu Val Asp Gly
            20                  25                  30


<210> SEQ ID NO 3
<211> LENGTH: 30
<212> TYPE: PRT
<213> ORGANISM: Artificial Sequence
<220> FEATURE:
<223> OTHER INFORMATION: the variant 2 of the Wild-type of the pH low
      insertion peptide

<400> SEQUENCE: 3

Ala Cys Glu Asp Gln Asn Pro Tyr Trp Arg Ala Tyr Ala Asp Leu Phe
1               5                   10                  15

Thr Pro Leu Thr Leu Leu Asp Leu Leu Ala Leu Trp Asp Gly
            20                  25                  30


<210> SEQ ID NO 4
<211> LENGTH: 27
<212> TYPE: PRT
<213> ORGANISM: Artificial Sequence
<220> FEATURE:
<223> OTHER INFORMATION: the variant 3 of the Wild-type of the pH low
      insertion peptide

<400> SEQUENCE: 4

Ala Cys Asp Asp Gln Asn Pro Trp Arg Ala Tyr Leu Asp Leu Leu Phe
1               5                   10                  15

Pro Thr Asp Thr Leu Leu Leu Asp Leu Leu Trp
            20                  25


<210> SEQ ID NO 5
<211> LENGTH: 27
<212> TYPE: PRT
<213> ORGANISM: Artificial Sequence
<220> FEATURE:
<223> OTHER INFORMATION: the variant 4 of the Wild-type of the pH low
      insertion peptide

<400> SEQUENCE: 5

Ala Cys Glu Glu Gln Asn Pro Trp Arg Ala Tyr Leu Glu Leu Leu Phe
1               5                   10                  15

Pro Thr Glu Thr Leu Leu Leu Glu Leu Leu Trp
            20                  25
```

```
<210> SEQ ID NO 6
<211> LENGTH: 25
<212> TYPE: PRT
<213> ORGANISM: Artificial Sequence
<220> FEATURE:
<223> OTHER INFORMATION: the variant 5 of the Wild-type of the pH low
      insertion peptide

<400> SEQUENCE: 6

Ala Cys Asp Asp Gln Asn Pro Trp Ala Arg Tyr Leu Asp Trp Leu Phe
1               5                   10                  15

Pro Thr Asp Thr Leu Leu Leu Asp Leu
            20                  25


<210> SEQ ID NO 7
<211> LENGTH: 24
<212> TYPE: PRT
<213> ORGANISM: Artificial Sequence
<220> FEATURE:
<223> OTHER INFORMATION: the variant 6 of the Wild-type of the pH low
      insertion peptide

<400> SEQUENCE: 7

Cys Asp Asn Asn Asn Pro Trp Arg Ala Tyr Leu Asp Leu Leu Phe Pro
1               5                   10                  15

Thr Asp Thr Leu Leu Leu Asp Trp
            20


<210> SEQ ID NO 8
<211> LENGTH: 25
<212> TYPE: PRT
<213> ORGANISM: Artificial Sequence
<220> FEATURE:
<223> OTHER INFORMATION: the variant 7 of the Wild-type of the pH low
      insertion peptide

<400> SEQUENCE: 8

Ala Cys Glu Glu Gln Asn Pro Trp Ala Arg Tyr Leu Glu Trp Leu Phe
1               5                   10                  15

Pro Thr Glu Thr Leu Leu Leu Glu Leu
            20                  25


<210> SEQ ID NO 9
<211> LENGTH: 24
<212> TYPE: PRT
<213> ORGANISM: Artificial Sequence
<220> FEATURE:
<223> OTHER INFORMATION: the variant 8 of the Wild-type of the pH low
      insertion peptide

<400> SEQUENCE: 9

Cys Glu Glu Gln Gln Pro Trp Ala Gln Tyr Leu Glu Leu Leu Phe Pro
1               5                   10                  15

Thr Glu Thr Leu Leu Leu Glu Trp
            20


<210> SEQ ID NO 10
<211> LENGTH: 24
<212> TYPE: PRT
<213> ORGANISM: Artificial Sequence
<220> FEATURE:
<223> OTHER INFORMATION: the variant 9 of the Wild-type of the pH low
      insertion peptide

<400> SEQUENCE: 10

Cys Glu Glu Gln Gln Pro Trp Arg Ala Tyr Leu Glu Leu Leu Phe Pro
```

-continued

```
1               5                   10                  15

Thr Glu Thr Leu Leu Leu Glu Trp
            20


<210> SEQ ID NO 11
<211> LENGTH: 24
<212> TYPE: PRT
<213> ORGANISM: Artificial Sequence
<220> FEATURE:
<223> OTHER INFORMATION: the variant 10 of the Wild-type of the pH low
      insertion peptide

<400> SEQUENCE: 11

Ala Cys Glu Asp Gln Asn Pro Trp Ala Arg Tyr Ala Asp Trp Leu Phe
1               5                   10                  15

Pro Thr Thr Leu Leu Leu Leu Asp
            20


<210> SEQ ID NO 12
<211> LENGTH: 24
<212> TYPE: PRT
<213> ORGANISM: Artificial Sequence
<220> FEATURE:
<223> OTHER INFORMATION: the variant 11 of the Wild-type of the pH low
      insertion peptide

<400> SEQUENCE: 12

Ala Cys Glu Glu Gln Asn Pro Trp Ala Arg Tyr Ala Glu Trp Leu Phe
1               5                   10                  15

Pro Thr Thr Leu Leu Leu Leu Glu
            20


<210> SEQ ID NO 13
<211> LENGTH: 22
<212> TYPE: PRT
<213> ORGANISM: Artificial Sequence
<220> FEATURE:
<223> OTHER INFORMATION: the variant 12 of the Wild-type of the pH low
      insertion peptide

<400> SEQUENCE: 13

Ala Cys Glu Asp Gln Asn Pro Trp Ala Arg Tyr Ala Asp Leu Leu Phe
1               5                   10                  15

Pro Thr Thr Leu Ala Trp
            20


<210> SEQ ID NO 14
<211> LENGTH: 22
<212> TYPE: PRT
<213> ORGANISM: Artificial Sequence
<220> FEATURE:
<223> OTHER INFORMATION: the variant 13 of the Wild-type of the pH low
      insertion peptide

<400> SEQUENCE: 14

Ala Cys Glu Glu Gln Asn Pro Trp Ala Arg Tyr Ala Glu Leu Leu Phe
1               5                   10                  15

Pro Thr Thr Leu Ala Trp
            20


<210> SEQ ID NO 15
<211> LENGTH: 34
<212> TYPE: PRT
<213> ORGANISM: Artificial Sequence
<220> FEATURE:
```

<223> OTHER INFORMATION: the variant 14 of the Wild-type of the pH low insertion peptide

<400> SEQUENCE: 15

```
Thr Glu Asp Ala Asp Val Leu Leu Ala Leu Asp Leu Leu Leu Leu Pro
1               5                   10                  15

Thr Thr Phe Leu Trp Asp Ala Tyr Arg Ala Trp Tyr Pro Asn Gln Glu
            20                  25                  30

Cys Ala
```

<210> SEQ ID NO 16
<211> LENGTH: 37
<212> TYPE: PRT
<213> ORGANISM: Artificial Sequence
<220> FEATURE:
<223> OTHER INFORMATION: the variant 15 of the Wild-type of the pH low insertion peptide

<400> SEQUENCE: 16

```
Cys Asp Asp Asp Asp Asp Asn Pro Asn Tyr Trp Ala Arg Tyr Ala Asn
1               5                   10                  15

Trp Leu Phe Thr Thr Pro Leu Leu Leu Leu Asn Gly Ala Leu Leu Val
            20                  25                  30

Glu Ala Glu Glu Thr
        35
```

<210> SEQ ID NO 17
<211> LENGTH: 37
<212> TYPE: PRT
<213> ORGANISM: Artificial Sequence
<220> FEATURE:
<223> OTHER INFORMATION: the variant 16 of the Wild-type of the pH low insertion peptide

<400> SEQUENCE: 17

```
Cys Asp Asp Asp Asp Asp Asn Pro Asn Tyr Trp Ala Arg Tyr Ala Pro
1               5                   10                  15

Trp Leu Phe Thr Thr Pro Leu Leu Leu Leu Pro Gly Ala Leu Leu Val
            20                  25                  30

Glu Ala Glu Glu Thr
        35
```

<210> SEQ ID NO 18
<211> LENGTH: 220
<212> TYPE: PRT
<213> ORGANISM: Mouse parvovirus 1

<400> SEQUENCE: 18

```
Phe Thr Ile Thr Ala Pro Lys Asp Leu Tyr Val Val Glu Tyr Gly Ser
1               5                   10                  15

Asn Val Thr Met Glu Cys Arg Phe Pro Val Glu Arg Glu Leu Asp Leu
            20                  25                  30

Leu Ala Leu Val Val Tyr Trp Glu Lys Glu Asp Glu Gln Val Ile Gln
        35                  40                  45

Phe Val Ala Gly Glu Glu Asp Leu Lys Pro Gln His Ser Asn Phe Arg
    50                  55                  60

Gly Arg Ala Ser Leu Pro Lys Asp Gln Leu Leu Lys Gly Asn Ala Ala
65                  70                  75                  80

Leu Gln Ile Thr Asp Val Lys Leu Gln Asp Ala Gly Val Tyr Cys Cys
                85                  90                  95
```

-continued

```
Ile Ile Ser Tyr Gly Gly Ala Asp Tyr Lys Arg Ile Thr Leu Lys Val
            100                 105                 110

Asn Ala Pro Tyr Arg Lys Ile Asn Gln Arg Ile Ser Val Asp Pro Ala
        115                 120                 125

Thr Ser Glu His Glu Leu Ile Cys Gln Ala Glu Gly Tyr Pro Glu Ala
    130                 135                 140

Glu Val Ile Trp Thr Asn Ser Asp His Gln Pro Val Ser Gly Lys Arg
145                 150                 155                 160

Ser Val Thr Thr Ser Arg Thr Glu Gly Met Leu Leu Asn Val Thr Ser
                165                 170                 175

Ser Leu Arg Val Asn Ala Thr Ala Asn Asp Val Phe Tyr Cys Thr Phe
            180                 185                 190

Trp Arg Ser Gln Pro Gly Gln Asn His Thr Ala Glu Leu Ile Ile Pro
        195                 200                 205

Glu Leu Pro Ala Thr His Pro Pro Gln Asn Arg Thr
    210                 215                 220


<210> SEQ ID NO 19
<211> LENGTH: 261
<212> TYPE: PRT
<213> ORGANISM: Homo sapiens

<400> SEQUENCE: 19

Phe Thr Val Thr Val Pro Lys Asp Leu Tyr Val Val Glu Tyr Gly Ser
1               5                   10                  15

Asn Met Thr Ile Glu Cys Lys Phe Pro Val Glu Lys Gln Leu Asp Leu
            20                  25                  30

Ala Ala Leu Ile Val Tyr Trp Glu Met Glu Asp Lys Asn Ile Ile Gln
        35                  40                  45

Phe Val His Gly Glu Glu Asp Leu Lys Val Gln His Ser Ser Tyr Arg
    50                  55                  60

Gln Arg Ala Arg Leu Leu Lys Asp Gln Leu Ser Leu Gly Asn Ala Ala
65                  70                  75                  80

Leu Gln Ile Thr Asp Val Lys Leu Gln Asp Ala Gly Val Tyr Arg Cys
                85                  90                  95

Met Ile Ser Tyr Gly Gly Ala Asp Tyr Lys Arg Ile Thr Val Lys Val
            100                 105                 110

Asn Ala Pro Tyr Asn Lys Ile Asn Gln Arg Ile Leu Val Val Asp Pro
        115                 120                 125

Val Thr Ser Glu His Glu Leu Thr Cys Gln Ala Glu Gly Tyr Pro Lys
    130                 135                 140

Ala Glu Val Ile Trp Thr Ser Ser Asp His Gln Val Leu Ser Gly Lys
145                 150                 155                 160

Thr Thr Thr Thr Asn Ser Lys Arg Glu Glu Lys Leu Phe Asn Val Thr
                165                 170                 175

Ser Thr Leu Arg Ile Asn Thr Thr Thr Asn Glu Ile Phe Tyr Cys Thr
            180                 185                 190

Phe Arg Arg Leu Asp Pro Glu Glu Asn His Thr Ala Glu Leu Val Ile
        195                 200                 205

Pro Glu Leu Pro Leu Ala His Pro Pro Asn Glu Arg Thr Gly Gly Gly
    210                 215                 220

Ser Ala Cys Glu Gln Asn Pro Ile Tyr Trp Ala Arg Tyr Ala Asp Trp
225                 230                 235                 240

Leu Phe Thr Thr Pro Leu Leu Leu Leu Asp Leu Ala Leu Leu Val Asp
                245                 250                 255
```

-continued

```
Ala Asp Glu Gly Thr
            260


<210> SEQ ID NO 20
<211> LENGTH: 260
<212> TYPE: PRT
<213> ORGANISM: Artificial Sequence
<220> FEATURE:
<223> OTHER INFORMATION: fusion protein for PDL1-WT pHLIP

<400> SEQUENCE: 20

Phe Thr Ile Thr Ala Pro Lys Asp Leu Tyr Val Val Glu Tyr Gly Ser
1               5                   10                  15

Asn Val Thr Met Glu Cys Arg Phe Pro Val Glu Arg Glu Leu Asp Leu
            20                  25                  30

Leu Ala Leu Val Val Tyr Trp Glu Lys Glu Asp Glu Gln Val Ile Gln
        35                  40                  45

Phe Val Ala Gly Glu Glu Asp Leu Lys Pro Gln His Ser Asn Phe Arg
    50                  55                  60

Gly Arg Ala Ser Leu Pro Lys Asp Gln Leu Leu Lys Gly Asn Ala Ala
65                  70                  75                  80

Leu Gln Ile Thr Asp Val Lys Leu Gln Asp Ala Gly Val Tyr Cys Cys
                85                  90                  95

Ile Ile Ser Tyr Gly Gly Ala Asp Tyr Lys Arg Ile Thr Leu Lys Val
            100                 105                 110

Asn Ala Pro Tyr Arg Lys Ile Asn Gln Arg Ile Ser Val Asp Pro Ala
        115                 120                 125

Thr Ser Glu His Glu Leu Ile Cys Gln Ala Glu Gly Tyr Pro Glu Ala
    130                 135                 140

Glu Val Ile Trp Thr Asn Ser Asp His Gln Pro Val Ser Gly Lys Arg
145                 150                 155                 160

Ser Val Thr Thr Ser Arg Thr Glu Gly Met Leu Leu Asn Val Thr Ser
                165                 170                 175

Ser Leu Arg Val Asn Ala Thr Ala Asn Asp Val Phe Tyr Cys Thr Phe
            180                 185                 190

Trp Arg Ser Gln Pro Gly Gln Asn His Thr Ala Glu Leu Ile Ile Pro
        195                 200                 205

Glu Leu Pro Ala Thr His Pro Pro Gln Asn Arg Thr Gly Gly Gly Ser
    210                 215                 220

Ala Cys Glu Gln Asn Pro Ile Tyr Trp Ala Arg Tyr Ala Asp Trp Leu
225                 230                 235                 240

Phe Thr Thr Pro Leu Leu Leu Leu Asp Leu Ala Leu Leu Val Asp Ala
                245                 250                 255

Asp Glu Gly Thr
            260


<210> SEQ ID NO 21
<211> LENGTH: 251
<212> TYPE: PRT
<213> ORGANISM: Artificial Sequence
<220> FEATURE:
<223> OTHER INFORMATION: fusion protein for PDL1-var3

<400> SEQUENCE: 21

Phe Thr Ile Thr Ala Pro Lys Asp Leu Tyr Val Val Glu Tyr Gly Ser
1               5                   10                  15

Asn Val Thr Met Glu Cys Arg Phe Pro Val Glu Arg Glu Leu Asp Leu
```

-continued

```
            20                  25                  30

Leu Ala Leu Val Val Tyr Trp Glu Lys Glu Asp Glu Gln Val Ile Gln
        35                  40                  45

Phe Val Ala Gly Glu Glu Asp Leu Lys Pro Gln His Ser Asn Phe Arg
    50                  55                  60

Gly Arg Ala Ser Leu Pro Lys Asp Gln Leu Leu Lys Gly Asn Ala Ala
65                  70                  75                  80

Leu Gln Ile Thr Asp Val Lys Leu Gln Asp Ala Gly Val Tyr Cys Cys
                85                  90                  95

Ile Ile Ser Tyr Gly Gly Ala Asp Tyr Lys Arg Ile Thr Leu Lys Val
            100                 105                 110

Asn Ala Pro Tyr Arg Lys Ile Asn Gln Arg Ile Ser Val Asp Pro Ala
        115                 120                 125

Thr Ser Glu His Glu Leu Ile Cys Gln Ala Glu Gly Tyr Pro Glu Ala
    130                 135                 140

Glu Val Ile Trp Thr Asn Ser Asp His Gln Pro Val Ser Gly Lys Arg
145                 150                 155                 160

Ser Val Thr Thr Ser Arg Thr Glu Gly Met Leu Leu Asn Val Thr Ser
                165                 170                 175

Ser Leu Arg Val Asn Ala Thr Ala Asn Asp Val Phe Tyr Cys Thr Phe
            180                 185                 190

Trp Arg Ser Gln Pro Gly Gln Asn His Thr Ala Glu Leu Ile Ile Pro
        195                 200                 205

Glu Leu Pro Ala Thr His Pro Pro Gln Asn Arg Thr Gly Gly Gly Ser
    210                 215                 220

Ala Cys Asp Asp Gln Asn Pro Trp Arg Ala Tyr Leu Asp Leu Leu Phe
225                 230                 235                 240

Pro Thr Asp Thr Leu Leu Leu Asp Leu Leu Trp
                245                 250


<210> SEQ ID NO 22
<211> LENGTH: 249
<212> TYPE: PRT
<213> ORGANISM: Artificial Sequence
<220> FEATURE:
<223> OTHER INFORMATION: fusion protein for PDL1-var7

<400> SEQUENCE: 22

Phe Thr Ile Thr Ala Pro Lys Asp Leu Tyr Val Val Glu Tyr Gly Ser
1               5                   10                  15

Asn Val Thr Met Glu Cys Arg Phe Pro Val Glu Arg Glu Leu Asp Leu
            20                  25                  30

Leu Ala Leu Val Val Tyr Trp Glu Lys Glu Asp Glu Gln Val Ile Gln
        35                  40                  45

Phe Val Ala Gly Glu Glu Asp Leu Lys Pro Gln His Ser Asn Phe Arg
    50                  55                  60

Gly Arg Ala Ser Leu Pro Lys Asp Gln Leu Leu Lys Gly Asn Ala Ala
65                  70                  75                  80

Leu Gln Ile Thr Asp Val Lys Leu Gln Asp Ala Gly Val Tyr Cys Cys
                85                  90                  95

Ile Ile Ser Tyr Gly Gly Ala Asp Tyr Lys Arg Ile Thr Leu Lys Val
            100                 105                 110

Asn Ala Pro Tyr Arg Lys Ile Asn Gln Arg Ile Ser Val Asp Pro Ala
        115                 120                 125

Thr Ser Glu His Glu Leu Ile Cys Gln Ala Glu Gly Tyr Pro Glu Ala
```

-continued

```
    130                 135                 140

Glu Val Ile Trp Thr Asn Ser Asp His Gln Pro Val Ser Gly Lys Arg
145                 150                 155                 160

Ser Val Thr Thr Ser Arg Thr Glu Gly Met Leu Leu Asn Val Thr Ser
                165                 170                 175

Ser Leu Arg Val Asn Ala Thr Ala Asn Asp Val Phe Tyr Cys Thr Phe
            180                 185                 190

Trp Arg Ser Gln Pro Gly Gln Asn His Thr Ala Glu Leu Ile Ile Pro
        195                 200                 205

Glu Leu Pro Ala Thr His Pro Pro Gln Asn Arg Thr Gly Gly Gly Ser
    210                 215                 220

Ala Cys Glu Glu Gln Asn Pro Trp Ala Arg Tyr Leu Glu Trp Leu Phe
225                 230                 235                 240

Pro Thr Glu Thr Leu Leu Leu Glu Leu
                245


<210> SEQ ID NO 23
<211> LENGTH: 783
<212> TYPE: DNA
<213> ORGANISM: Artificial Sequence
<220> FEATURE:
<223> OTHER INFORMATION: Nucleic acid encoding the fusion protein for
      PDL1-WT pHLIP

<400> SEQUENCE: 23

tttaccatta ccgcgccgaa agatctgtat gtggtggaat atggcagcaa cgtgaccatg     60

gaatgccgtt ttccggtgga acgtgaactg gatctgctgg cgctggtggt gtattgggaa    120

aaagaagatg aacaggtgat tcagtttgtg gcgggcgaag aagatctgaa accgcagcat    180

agcaactttc gtggccgtgc gagcctgccg aaagatcagc tgctgaaagg caacgcggcg    240

ctgcagatta ccgatgtgaa actgcaggat gcgggcgtgt attgctgcat tattagctat    300

ggcggcgcgg attataaacg tattaccctg aaagtgaacg cgccgtatcg taaaattaac    360

cagcgtatta gcgtggaccc ggcgaccagc gaacatgaac tgatttgcca ggcggaaggc    420

tatccggaag cggaagtgat ttggaccaac agcgatcatc agccggtgag cggcaaacgt    480

agcgtgacca ccagccgtac cgaaggcatg ctgctgaacg tgaccagcag cctgcgtgtg    540

aacgcgaccg cgaacgatgt gttttattgc accttttggc gtagccagcc gggccagaac    600

cataccgcgg aactgattat tccggaactg ccggcgaccc atccgccgca gaaccgtacc    660

ggcggcggca gcgcctgcga gcagaacccc atctactggg ccaggtacgc cgactggctg    720

ttcaccaccc ccctgctgct gctggacctg gccctgctgg tggacgccga cgagggcacc    780

taa                                                                  783


<210> SEQ ID NO 24
<211> LENGTH: 756
<212> TYPE: DNA
<213> ORGANISM: Artificial Sequence
<220> FEATURE:
<223> OTHER INFORMATION: Nucleic acid encoding the fusion protein for
      PDL1-var3

<400> SEQUENCE: 24

tttaccatta ccgcgccgaa agatctgtat gtggtggaat atggcagcaa cgtgaccatg     60

gaatgccgtt ttccggtgga acgtgaactg gatctgctgg cgctggtggt gtattgggaa    120

aaagaagatg aacaggtgat tcagtttgtg gcgggcgaag aagatctgaa accgcagcat    180
```

```
agcaactttc gtggccgtgc gagcctgccg aaagatcagc tgctgaaagg caacgcggcg    240

ctgcagatta ccgatgtgaa actgcaggat gcgggcgtgt attgctgcat tattagctat    300

ggcggcgcgg attataaacg tattaccctg aaagtgaacg cgccgtatcg taaaattaac    360

cagcgtatta gcgtggaccc ggcgaccagc gaacatgaac tgatttgcca ggcggaaggc    420

tatccggaag cggaagtgat ttggaccaac agcgatcatc agccggtgag cggcaaacgt    480

agcgtgacca ccagccgtac cgaaggcatg ctgctgaacg tgaccagcag cctgcgtgtg    540

aacgcgaccg cgaacgatgt gttttattgc accttttggc gtagccagcc gggccagaac    600

cataccgcgg aactgattat tccggaactg ccggcgaccc atccgccgca gaaccgtacc    660

ggcggcggca gcgcctgcga cgaccagaac ccctggaggg cctacctgga cctgctgttc    720

cccaccgaca ccctgctgct ggacctgctg tggtaa                              756
```

```
<210> SEQ ID NO 25
<211> LENGTH: 750
<212> TYPE: DNA
<213> ORGANISM: Artificial Sequence
<220> FEATURE:
<223> OTHER INFORMATION: Nucleic acid encoding the fusion protein for
      PDL1-var7

<400> SEQUENCE: 25

tttaccatta ccgcgccgaa agatctgtat gtggtggaat atggcagcaa cgtgaccatg     60

gaatgccgtt ttccggtgga acgtgaactg gatctgctgg cgctggtggt gtattgggaa    120

aaagaagatg aacaggtgat tcagtttgtg gcgggcgaag aagatctgaa accgcagcat    180

agcaactttc gtggccgtgc gagcctgccg aaagatcagc tgctgaaagg caacgcggcg    240

ctgcagatta ccgatgtgaa actgcaggat gcgggcgtgt attgctgcat tattagctat    300

ggcggcgcgg attataaacg tattaccctg aaagtgaacg cgccgtatcg taaaattaac    360

cagcgtatta gcgtggaccc ggcgaccagc gaacatgaac tgatttgcca ggcggaaggc    420

tatccggaag cggaagtgat ttggaccaac agcgatcatc agccggtgag cggcaaacgt    480

agcgtgacca ccagccgtac cgaaggcatg ctgctgaacg tgaccagcag cctgcgtgtg    540

aacgcgaccg cgaacgatgt gttttattgc accttttggc gtagccagcc gggccagaac    600

cataccgcgg aactgattat tccggaactg ccggcgaccc atccgccgca gaaccgtacc    660

ggcggcggca gcgcctgcga ggagcagaac ccctgggcca ggtacctgga gtggctgttc    720

cccaccgaga ccctgctgct ggagctgtaa                                     750
```

```
<210> SEQ ID NO 26
<211> LENGTH: 660
<212> TYPE: DNA
<213> ORGANISM: Artificial Sequence
<220> FEATURE:
<223> OTHER INFORMATION: Nucleic acid encoding the extracellular domain
      of mouse PDL1

<400> SEQUENCE: 26

tttaccatta ccgcgccgaa agatctgtat gtggtggaat atggcagcaa cgtgaccatg     60

gaatgccgtt ttccggtgga acgtgaactg gatctgctgg cgctggtggt gtattgggaa    120

aaagaagatg aacaggtgat tcagtttgtg gcgggcgaag aagatctgaa accgcagcat    180

agcaactttc gtggccgtgc gagcctgccg aaagatcagc tgctgaaagg caacgcggcg    240

ctgcagatta ccgatgtgaa actgcaggat gcgggcgtgt attgctgcat tattagctat    300

ggcggcgcgg attataaacg tattaccctg aaagtgaacg cgccgtatcg taaaattaac    360
```

-continued cagcgtatta gcgtggaccc ggcgaccagc gaacatgaac tgatttgcca ggcggaaggc 420
tatccggaag cggaagtgat ttggaccaac agcgatcatc agccggtgag cggcaaacgt 480
agcgtgacca ccagccgtac cgaaggcatg ctgctgaacg tgaccagcag cctgcgtgtg 540
aacgcgaccg cgaacgatgt gttttattgc accttttggc gtagccagcc gggccagaac 600
cataccgcgg aactgattat tccggaactg ccggcgaccc atccgccgca gaaccgtacc 660

<210> SEQ ID NO 27
<211> LENGTH: 459
<212> TYPE: PRT
<213> ORGANISM: Artificial Sequence
<220> FEATURE:
<223> OTHER INFORMATION: fusion protein for PDL1-Ig

<400> SEQUENCE: 27

Phe Thr Ile Thr Ala Pro Lys Asp Leu Tyr Val Val Glu Tyr Gly Ser
1               5                   10                  15

Asn Val Thr Met Glu Cys Arg Phe Pro Val Glu Arg Glu Leu Asp Leu
            20                  25                  30

Leu Ala Leu Val Val Tyr Trp Glu Lys Glu Asp Glu Gln Val Ile Gln
        35                  40                  45

Phe Val Ala Gly Glu Glu Asp Leu Lys Pro Gln His Ser Asn Phe Arg
    50                  55                  60

Gly Arg Ala Ser Leu Pro Lys Asp Gln Leu Leu Lys Gly Asn Ala Ala
65                  70                  75                  80

Leu Gln Ile Thr Asp Val Lys Leu Gln Asp Ala Gly Val Tyr Cys Cys
                85                  90                  95

Ile Ile Ser Tyr Gly Gly Ala Asp Tyr Lys Arg Ile Thr Leu Lys Val
            100                 105                 110

Asn Ala Pro Tyr Arg Lys Ile Asn Gln Arg Ile Ser Val Asp Pro Ala
        115                 120                 125

Thr Ser Glu His Glu Leu Ile Cys Gln Ala Glu Gly Tyr Pro Glu Ala
    130                 135                 140

Glu Val Ile Trp Thr Asn Ser Asp His Gln Pro Val Ser Gly Lys Arg
145                 150                 155                 160

Ser Val Thr Thr Ser Arg Thr Glu Gly Met Leu Leu Asn Val Thr Ser
                165                 170                 175

Ser Leu Arg Val Asn Ala Thr Ala Asn Asp Val Phe Tyr Cys Thr Phe
            180                 185                 190

Trp Arg Ser Gln Pro Gly Gln Asn His Thr Ala Glu Leu Ile Ile Pro
        195                 200                 205

Glu Leu Pro Ala Thr His Pro Pro Gln Asn Arg Thr Gly Gly Gly Gly
    210                 215                 220

Gly Ser Glu Pro Arg Gly Pro Thr Ile Lys Pro Cys Pro Pro Cys Lys
225                 230                 235                 240

Cys Pro Ala Pro Asn Leu Leu Gly Gly Pro Ser Val Phe Ile Phe Pro
                245                 250                 255

Pro Lys Ile Lys Asp Val Leu Met Ile Ser Leu Ser Pro Ile Val Thr
            260                 265                 270

Cys Val Val Val Asp Val Ser Glu Asp Asp Pro Asp Val Gln Ile Ser
        275                 280                 285

Trp Phe Val Asn Asn Val Glu Val His Thr Ala Gln Thr Gln Thr His
    290                 295                 300

Arg Glu Asp Tyr Asn Ser Thr Leu Arg Val Val Ser Ala Leu Pro Ile

-continued

```
305                 310                 315                 320

Gln His Gln Asp Trp Met Ser Gly Lys Glu Phe Lys Cys Lys Val Asn
                325                 330                 335

Asn Lys Asp Leu Pro Ala Pro Ile Glu Arg Thr Ile Ser Lys Pro Lys
            340                 345                 350

Gly Ser Val Arg Ala Pro Gln Val Tyr Val Leu Pro Pro Pro Glu Glu
        355                 360                 365

Glu Met Thr Lys Lys Gln Val Thr Leu Thr Cys Met Val Thr Asp Phe
    370                 375                 380

Met Pro Glu Asp Ile Tyr Val Glu Trp Thr Asn Asn Gly Lys Thr Glu
385                 390                 395                 400

Leu Asn Tyr Lys Asn Thr Glu Pro Val Leu Asp Ser Asp Gly Ser Tyr
                405                 410                 415

Phe Met Tyr Ser Lys Leu Arg Val Glu Lys Lys Asn Trp Val Glu Arg
            420                 425                 430

Asn Ser Tyr Ser Cys Ser Val Val His Glu Gly Leu His Asn His His
        435                 440                 445

Thr Thr Lys Ser Phe Ser Arg Thr Pro Gly Lys
    450                 455


<210> SEQ ID NO 28
<211> LENGTH: 1380
<212> TYPE: DNA
<213> ORGANISM: Artificial Sequence
<220> FEATURE:
<223> OTHER INFORMATION: Nucleic acid encoding the fusion protein for
      PDL1-Ig

<400> SEQUENCE: 28

tttaccatta ccgcgccgaa agatctgtat gtggtggaat atggcagcaa cgtgaccatg     60

gaatgccgtt ttccggtgga acgtgaactg gatctgctgg cgctggtggt gtattgggaa    120

aaagaagatg aacaggtgat tcagtttgtg gcgggcgaag aagatctgaa accgcagcat    180

agcaactttc gtggccgtgc gagcctgccg aaagatcagc tgctgaaagg caacgcggcg    240

ctgcagatta ccgatgtgaa actgcaggat gcgggcgtgt attgctgcat tattagctat    300

ggcggcgcgg attataaacg tattaccctg aaagtgaacg cgccgtatcg taaaattaac    360

cagcgtatta gcgtggaccc ggcgaccagc gaacatgaac tgatttgcca ggcggaaggc    420

tatccggaag cggaagtgat ttggaccaac agcgatcatc agccggtgag cggcaaacgt    480

agcgtgacca ccagccgtac cgaaggcatg ctgctgaacg tgaccagcag cctgcgtgtg    540

aacgcgaccg cgaacgatgt gttttattgc accttttggc gtagccagcc gggccagaac    600

cataccgcgg aactgattat tccggaactg ccggcgaccc atccgccgca gaaccgtacc    660

ggcggcggcg gcggatccga gcccagaggg cccacaatca agccctgtcc tccatgcaaa    720

tgcccagcac ctaacctctt gggtggacca tccgtcttca tcttccctcc aaagatcaag    780

gatgtactca tgatctccct gagccccata gtcacatgtg tggtggtgga tgtgagcgag    840

gatgacccag atgtccagat cagctggttt gtgaacaacg tggaagtaca cacagctcag    900

acacaaaccc atagagagga ttacaacagt actctccggg tggtcagtgc cctccccatc    960

cagcaccagg actggatgag tggcaaggag ttcaaatgca aggtcaacaa caaagacctc   1020

ccagcgccca tcgagagaac catctcaaaa cccaaagggt cagtaagagc tccacaggta   1080

tatgtcttgc ctccaccaga agaagagatg actaagaaac aggtcactct gacctgcatg   1140

gtcacagact tcatgcctga agacatttac gtggagtgga ccaacaacgg gaaaacagag   1200
```

-continued

```
ctaaactaca agaacactga accagtcctg gactctgatg gttcttactt catgtacagc   1260

aagctgagag tggaaaagaa gaactgggtg gaaagaaata gctactcctg ttcagtggtc   1320

cacgagggtc tgcacaatca ccacacgact aagagcttct cccggactcc gggtaaataa   1380


<210> SEQ ID NO 29
<211> LENGTH: 4
<212> TYPE: PRT
<213> ORGANISM: Artificial Sequence
<220> FEATURE:
<223> OTHER INFORMATION: synthesized

<400> SEQUENCE: 29

Gly Gly Gly Ser
1


<210> SEQ ID NO 30
<211> LENGTH: 5
<212> TYPE: PRT
<213> ORGANISM: Artificial Sequence
<220> FEATURE:
<223> OTHER INFORMATION: synthesized

<400> SEQUENCE: 30

Gly Gly Gly Gly Ser
1               5
```

FUSION PEPTIDE FOR TREATING AUTOIMMUNE DISEASE

INCORPORATION OF SEQUENCE LISTING

This application contains a sequence listing submitted in Computer Readable Form (CRF). The CFR file containing the sequence listing entitled "PA630.0005_ST25.txt", which was created on Dec. 26, 2025, and is 28,943 bytes in size. The information in the sequence listing is incorporated herein by reference in its entirety.

TECHNICAL FIELD

The present invention belongs to the field of biological medicine, and more particularly relates to a fusion peptide for treating autoimmune diseases.

BACKGROUND ART

Autoimmune diseases are mainly auto-histologic lesion initiated diseases caused by immune response of the body to autoantigen, a large number of immune cell infiltration and metabolic disorders of immune tissues.

According to the scope of pathological tissues, the autoimmune diseases may be divided into two main categories. The first category refers to organ specific autoimmune diseases and may involve multiple organs including the brain, thyroid and stomach; and the second category refers to non-organ specific autoimmune diseases and may involve multiple tissues including muscles, skin and joints. There are more than 100 currently known autoimmune diseases that involve about 5% of the population. Common autoimmune diseases include systemic lupus erythematosus, rheumatoid arthritis, systemic vasculitis and scleroderma.

To ensure basic response of life, the life system generally has a strictly controlled chemical environment. In normal cells of healthy tissues, the pH inside and outside the cells is generally relatively constant. The pH outside the cells is 7.4. However, at lesion sites of the autoimmune diseases, a local lactate concentration is sharply increased due to great infiltration and hypermetabolism of inflammatory immune cells; the balance is disturbed; the pH outside the cells is generally 6.2-7.0; and then an acidic extracellular microenvironment is produced. A pH low insertion peptide (pHLIP) from a trans membrane helical protein C of bacteriorhodopsin happens to be a peptide carrier that can target the slightly acidic environment. The pHLIP is composed of a flanking sequence and a trans membrane (TM) sequence, wherein the flanking sequence is composed of protonated amino acid residues; and the TM sequence is composed of hydrophobic residues. The pHLIP does not form a single helix of the trans membrane in a neutral solution. However, the pHLIP may form a C-helix structure in an acid solution in the presence of lipid bilayer, and then is inserted onto the cell membrane.

The pHLIP generally has three states. In healthy tissues having the pH value of about 7.4, the pHLIP is in a dissolved state (state I) or is weakly bound to the membrane (state II). The pHLIP is rinsed from the membrane through normal perfusion, and continuously circulates through the body. In inflammation tissues having the acidic pH value, the pHLIP spontaneously folds into a trans membrane helix to be inserted onto the membrane (state III).

At present, the pHLIP has very wide applications in nuclear imaging, fluorescence-guided surgery, gene therapy and nanotechnology. Trend development of drugs for treating the autoimmune diseases by utilizing the acidic environment of the pHLIP is a research hotspot in the future.

SUMMARY OF THE INVENTION

The present invention is achieved based on the concept as follows: an extracellular domain of PD-L1 is bound to an N terminal of pHLIP; the extracellular domain of the PD-L1 is shown on a tissue cell membrane of a lesion site through the pHLIP; a PD-1/PD-L1 negative signal of the focus tissue is enhanced by utilizing the pHLIP; and immune response of effector T cells is suppressed at the source, thereby achieving an effect of preventing and treating occurrence and development of the autoimmune diseases.

A first purpose of the present invention is to provide a fusion peptide formed by PD-L1 and a pH low insertion peptide.

A second purpose of the present invention is to provide a pharmaceutical composition for treating autoimmune diseases formed by the above fusion peptide.

A third purpose of the present invention is to provide an application of the above fusion peptide.

To achieve the above purposes, technical solutions of the present invention are as follows:

According to one aspect of the present invention, the present invention provides a fusion peptide of a pH low insertion peptide, wherein the fusion peptide includes the pH low insertion peptide, an immune checkpoint ligand or fragments thereof.

Immune checkpoints include PD-1, Lag-3, Tim-3, TIGIT and CTLA-4.

APD-1 ligand includes PD-L1 and PD-L2.

A Lag-3 ligand includes a fibrinogen-like protein 1 and LSECtin.

A Tim-3 ligand includes galectin-9, phosphatidylserine, a high-mobility group protein B1 and Ceacam-1.

A TIGIT ligand includes CD155 and CD122.

A CTLA-4 ligand includes CD86(B7-2) and CD80(B7-1).

The pH low insertion peptide that can be used for constructing the fusion peptide in the present invention includes a peptide having a sequence shown as SEQ ID NO: 1 or variants thereof.

The peptide having the sequence shown as SEQ ID NO: 1 is called WT for short in the present invention. The variants of the WT include Var1-Var16.

The sequences of the WT and the variants thereof are as follows:

WT:
(SEQ ID NO: 1)
ACEQNPIYWARYADWLFTTPLLLLDLALLVDADEGT;

Var1:
(SEQ ID NO: 2)
ACEDQNPYWARYADWLFTTPLLLLDLALLVDG;

Var2:
(SEQ ID NO: 3)
ACEDQNPYWRAYADLFTPLTLLDLLALWDG;

Var3:
(SEQ ID NO: 4)
ACDDQNPWRAYLDLLFPTDTLLLDLLW;

Var4:
(SEQ ID NO: 5)
ACEEQNPWRAYLELLFPTETLLLELLW;

-continued

Var5:
(SEQ ID NO: 6)
ACDDQNPWARYLDWLFPTDTLLLDL;

Var6:
(SEQ ID NO: 7)
CDNNNPWRAYLDLLFPTDTLLLDW;

Var7:
(SEQ ID NO: 8)
ACEEQNPWARYLEWLFPTETLLLEL;

Var8:
(SEQ ID NO: 9)
CEEQQPWAQYLELLFPTETLLLEW;

Var9:
(SEQ ID NO: 10)
CEEQQPWRAYLELLFPTETLLLEW;

Var10:
(SEQ ID NO: 11)
ACEDQNPWARYADWLFPTTLLLLD;

Var11:
(SEQ ID NO: 12)
ACEEQNPWARYAEWLFPTTLLLLE;

Var12:
(SEQ ID NO: 13)
ACEDQNPWARYADLLFPTTLAW;

Var13:
(SEQ ID NO: 14)
ACEEQNPWARYAELLFPTTLAW;

Var14:
(SEQ ID NO: 15)
TEDADVLLALDLLLLPTTFLWDAYRAWYPNQECA;

Var15:
(SEQ ID NO: 16)
CDDDDDNPNYWARYANWLFTTPLLLLNGALLVEAEET;

Var16:
(SEQ ID NO: 17)
CDDDDDNPNYWARYAPWLFTTPLLLLPGALLVEAEET.

The above underlined parts represent extracellular domains of the pH low insertion peptide.

Peptides ((extracellular domain) n+ pH low insertion peptide, wherein n=1, 2, 3 . . . ) formed by repeating the extracellular domains of the peptides such as the WT and the Var1-Var16 once or for many times also belong to the scope of the pH low insertion peptide in the present invention.

The PD-L1 protein or a fragment thereof in the present invention is bound to the N terminal of the pH low insertion peptide through Linker.

The Linker is commonly used in the art; and a sequence may be SEQ ID NO: 29: (GGGS)m or SEQ ID NO: 30: (GGGGS)m, wherein m=natural number.

Preferably, the sequence of the Linker is GGGS, SEQ ID NO: 29.

In one specific implementation solution of the present invention, the used immune checkpoint is PD-1, and the selected ligand is PD-L1.

In specific embodiments of the present invention, the PD-L1 fragment bound to the sequence of the pH low insertion peptide is an extracellular domain of the PD-L1 protein.

Further, a sequence of the extracellular domain of the PD-L1 protein is shown as SEQ ID NO: 18 or SEQ ID NO: 19. Peptides derived from the amino acid sequence shown as SEQ ID NO: 18 or SEQ ID NO: 19 that are subjected to substitution and/or deletion and/or addition of one or several amino acid residues in the amino acid sequence shown as SEQ ID NO: 18 or SEQ ID NO: 19 and that have the same function as the sequence shown as SEQ ID NO: 18 or SEQ ID NO: 19 also belong to the extracellular domain of the PD-L1 protein, i.e., the extracellular domain of the PD-L1 protein in the present invention includes a wild type and variants thereof.

The variants of the extracellular domain of the PD-L1 protein have at least 80% of homology (also called sequence identity) with the amino acid sequence shown as SEQ ID NO: 18 or SEQ ID NO: 19, more preferably, have at least about 90-95% of homology with the amino acid sequence shown as SEQ ID NO: 18 or SEQ ID NO: 19, generally homology of 96%, 97%, 98% and 99%.

Generally it is known that, functions of the protein will not be affected by modification of one or more amino acids in one protein or peptide. Those skilled in the art may recognize that, change of a single amino acid or a small percentage of amino acids or individual addition, deletion, insertion and substitution of the amino acid sequence may be conservative modification. Due to the change of the protein or peptide, proteins or peptides having similar functions are produced. Providing a conservative substitution table of amino acids having similar functions is well known in the art.

The variants of the extracellular domain of the PD-L1 protein also include non-conservative modification of the amino acid sequence shown as SEQ ID NO: 18 or SEQ ID NO: 19, as long as the modified peptide can still remain biological activity of the bound ligand.

The fusion peptide constructed by utilizing the extracellular domain of the PD-L1 protein and the pH low insertion peptide is expressed as follows: in specific embodiments of the present invention, an amino acid sequence of PDL1-WTpHLIP is shown as SEQ ID NO: 20; in specific embodiments of the present invention, an amino acid sequence of PDL1-var3 is shown as SEQ ID NO: 21; and in specific embodiments of the present invention, an amino acid sequence of PDL1-var7 is shown as SEQ ID NO: 22.

According to another aspect of the present invention, the present invention provides a pharmaceutical composition for treating autoimmune diseases. The pharmaceutical composition includes the above fusion peptide.

Further, the pharmaceutical composition further includes pharmaceutically acceptable carriers.

Examples of the pharmaceutically acceptable carriers include but are not limited to water; water carriers, such as but not limited to sodium chloride injection, Ringer's injection, glucose injection, glucose and sodium chloride injection and lactated Ringer's injection; water miscible carriers, such as but not limited to ethanol, polyethylene glycol and polypropylene glycol; and non-aqueous carriers, such as but not limited to corn oil, cottonseed oil, peanut oil, sesame oil, ethyl oleate, isopropyl myristate and benzyl benzoate.

Further, the pharmaceutical composition further includes other drugs used for treating the autoimmune diseases.

The pharmaceutical composition in the present invention may be administered to human patients in any pathway. These pathways include but are not limited to: intravenous, intracutaneous, transdermal, subcutaneous, intramuscular, inhalation (e.g., by aerosol), oral (e.g., sublingual), local (e.g., skin and mucosal surfaces, including airway surface), intrathecal, intra-articular, intrapleural, intracerebral, intra-artery, intraperitoneal, oral, intra-lymphatic, intranasal, rectal or vaginal administration. The composition is subjected to local catheter perfusion or intra-lesional direct injection. In one implementation mode, the composition in the present invention is administered through intravenous transfusion or intravenous infusion within given time (0.5-2 hours). The pharmaceutical composition in the present invention may be delivered through a peristaltic pump or in the form of a long-acting preparation. However, as understood in the art, the most appropriate pathway in any given situation depends on factors as follows: types, ages, genders and overall physical conditions of objects, characteristics and severity of the treated diseases, and/or characteristics of the specific given composition (e.g., dose and dosage form). In specific implementation modes, the administration route is transfusion or continuous infusion once a week or twice a week over a period of time. In other specific implementation modes, the administration route is subcutaneous injection, optionally once or twice a week. In one implementation mode, the pharmaceutical composition in the present invention is administered to outpatients.

In some implementation modes, the dose of the pharmaceutical composition in the present invention is counted by taking weight of the patients (mg/kg) as a unit. In other implementation modes, the dose of the pharmaceutical composition is counted by taking the body surface area of the patients (mg/$m^2$) as a unit. In other implementation modes, the dose of the pharmaceutical composition is counted by taking the dose to the patients (mg/) as a unit. Any dose measuring method may be used in combination with the composition and method in the present invention; and the dose unit may be converted through a standard mode in the art.

Those skilled in the art should understand that, the dose may be selected according to multiple factors, including the ages, genders, types and diseases of the objects. The needed cell consumption degree and the dose may be determined by those skilled in the art. For example, an effective dose of the pharmaceutical composition may be extrapolated through a dose-response curve from an in-vitro detection system or an animal model detection system.

Those skilled in the art should understand that, compared with a maintenance solution, the dose of initial treatment is generally higher and/or an administration frequency is higher.

According to another aspect of the present invention, the present invention provides an application of an immune checkpoint ligand or fragments thereof in preparation of the above fusion peptide.

Restriction of the immune checkpoint ligand or fragments thereof is the same as above.

According to another aspect of the present invention, the present invention provides an application of the above fusion peptide in preparation of drugs for treating autoimmune diseases.

The term "autoimmune diseases" refers to object diseases of cell, tissue and/or organ damage caused by immune response of feature objects to the own cells, tissues and/or organs. Exemplary autoimmune diseases include alopecia areata, ankylosing spondylitis, antiphospholipide syndrome, autoimmune Addison's disease, autoimmune disease of the adrenal gland, autoimmune hemolytic anemia, autoimmune hepatitis, autoimmune oophoritis and orchitis, autoimmune thrombocytopenia, Behcet's syndrome, bullous pemphigoid, cardiomyopathy, oral inflammatory diarrhea dermatitis, chronic fatigue immunologic inadequacy syndrome, chronic inflammatory demyelinating polyneuropathy, Chusch-Schotter's syndrome, cicatricial pemphigoid, CREST syndrome, cold hemagglutinin disease, Crohn's disease, discoid lupus erythematosus, idiopathic mixed cryoglobulinemia, diabetes, eosinophilic fasciitis, fibromyalgia-fibromyositis, glomerulonephritis, Graves' disease, Guillain-Barre syndrome, hashimoto thyroiditis, purpura Henoch-Schonlein, idiopathic pulmonary fibrosis, idiopathic/autoimmune thrombocytopenic purpura, IgA neuropathy, juvenile arthritis, lichen planus, lupus erythematosus, Meniere's syndrome, mixed connective tissue disease, disseminated sclerosis, type 1 or immune-mediated diabetes, myasthenia gravis, pemphigus-related diseases, pernicious anemia, polyarteritis nodosa, polychondritis, polyglandular syndrome, polymyalgia rheumatic, polymyositis, dermatomyositis, primary agammaglobulinemia, primary biliary cirrhosis, psoriasis, psoriatic arthritis, Raynaud phenomenon, Reiter syndrome, rheumatoid arthritis, nodule disease, scleroderma, Sjogren syndrome, stiff-man syndrome, systemic lupus erythematosus, Sweet's syndrome, Still's disease, lupus erythematosus, Takayasu's arteritis, transient arteritis/giant cell arteritis, ulcerative colitis, uveitis, vasculitis, leucoderma and Wegener's granulomatosis.

Further, the drugs include the above pharmaceutical composition.

The drugs or pharmaceutical composition in the present invention may be used in combination with other drugs for treating the autoimmune diseases.

Common drugs for treating rheumatoid arthritis include NSAID (non-restrictive examples include but are not limited to: aspirin, diflunisal, diclofenac, etodolac, fenamates, fenoprofen, flurbiprofen, ibuprofen, indometacin, ketoprofen, methyl salicylate, nabumetone, naproxen, piperazine, butazodine, piroxicam, sulindac and tolmetin); analgesics (non-restrictive examples including acetaminophen, phenacetin and Tramadol); CSI, including but not limited to celecoxib and rofecoxib; glucocorticoids (preferably, low-dose oral glucocorticoids, <7.5 mg/d metacortandracin, or high-dose glucocorticoids subjected to pulsatile delivery per month, or intra-articular glucocorticoids); disease-modifying antirheumatic drugs (DMARD), including but not limited to amethopterin (preferably, given intermittently low dose, e.g., 7.5-30 mg once a week), gold compounds (such as gold salts), D-penicillamine, antimalarial (such as chloroquine) and salazosulfapyridine; TNF-α neutralizers, including but not limited to etanercept and infliximab; and immunosuppressors and cytotoxic agents (examples including but not limited to: azathioprine, leflunomide, cyclosporine and cyclophosphamide).

Common drugs for treating osteoarthritis include but not limited to: analgesics (non-restrictive examples include acetaminophen at a dose of 4000 mg/d; phenacetin; and Tramadol having a daily dose of 200-300 mg); and NSAID (non-restrictive examples include but are not limited to: aspirin, diflunisal, diclofenac, etodolac, fenamates, fenoprofen, flurbiprofen, ibuprofen, indometacin, ketoprofen, methyl salicylate, nabumetone, naproxen, piperazine, butazodine, piroxicam, sulindac and tolmetin), preferably low-dose NSAID such as 1200 mg/d of ibuprofen and 500 mg/d of naproxen. A gastric protective agent such as misoprostol, famotidine or omeprazole is preferably simultaneously used with the NSAID. Non-acetylated salicylate includes but not limited to salsalate. Cyclo-oxygenase (Cox)-2-specific inhibitors (CSI) include but not limited to celecoxib and rofecoxib; long-acting glucocorticoid preparations, hyaluronic acid and capsaicin cream.

According to another aspect of the present invention, the present invention provides a marker system. The marker system includes the above fusion peptide.

Further, the marker system may further include Cyanine 5.5, ALEXA FLUOR® 750, ALEXA FLUOR® 647, ALEXA FLUOR® 488, ALEXA FLUOR® 546, $^{64}$Cu- DOTA, $^{68}$Ga-DOTA, $^{18}$F-O-pyridine, $^{18}$F-liposomes, liposomal Rhodamine, NANOGOLD® and TAMRA.

The fusion peptide in the marker system is inserted onto the cell membrane under the effect of the pH low insertion peptide; the PDL1 in the fusion peptide is localized on the surface of target cells; the PDL1 on the surface of the target cells is recognized by a PDL1 ligand (such as PD-1) on the surface of immune cells; and the PDL1 ligand is bound to the PDL1, thereby suppressing immune cell functions.

According to another aspect of the present invention, the present invention provides an application of the above fusion peptide in preparation of an autoimmune disease focus tissue cell marker system. Further, the marker system is the same as above.

According to another aspect of the present invention, the present invention provides a method for treating autoimmune diseases. The treatment method includes: applying the above fusion peptide or the above pharmaceutical composition in the present invention to patients in need.

According to another aspect of the present invention, the present invention provides a method for marking an immune checkpoint ligand or fragments thereof on a focus tissue cell membrane. The method includes: binding the immune checkpoint ligand or fragments thereof to a pH low insertion peptide to form a fusion peptide.

Further, the method also includes: introducing the fusion peptide into the focus tissue and inserting onto the focus tissue cell membrane.

The immune checkpoints include the above immune checkpoints; the immune checkpoint ligand includes the above immune checkpoint ligand; and the fragments of the immune checkpoint ligand include the above fragments of the immune checkpoint ligand.

The pH low insertion peptide includes the above pH low insertion peptide.

According to another aspect of the present invention, the present invention provides an application of the immune checkpoint ligand or fragments thereof in preparation of drugs for treating autoimmune diseases.

Further, the immune checkpoints include the above immune checkpoints; the immune checkpoint ligand includes the above immune checkpoint ligand; and the fragments of the immune checkpoint ligand include the above fragments of the immune checkpoint ligand.

Further, restriction of the autoimmune diseases is the same as above.

Further, the drugs include the above pharmaceutical composition.

According to another aspect of the present invention, the present invention provides an application of the immune checkpoint ligand or fragments thereof in preparation of an autoimmune disease focus tissue cell marker system.

Further, the immune checkpoints include the above immune checkpoints; the immune checkpoint ligand includes the above immune checkpoint ligand; and the fragments of the immune checkpoint ligand include the above fragments of the immune checkpoint ligand.

Further, the marker system includes the above marker system.

According to another aspect of the present invention, the present invention provides an application of the pH low insertion peptide in preparation of the above fusion peptide.

Further, restriction of the pH low insertion peptide is the same as above.

According to another aspect of the present invention, the present invention provides an application of the pH low insertion peptide in preparation of drugs for treating autoimmune diseases.

Further, restriction of the pH low insertion peptide is the same as above.

Further, restriction of the autoimmune diseases is the same as above.

Further, the drugs include the above pharmaceutical composition.

According to another aspect of the present invention, the present invention provides an application of the pH low insertion peptide in preparation of an autoimmune disease focus tissue cell marker system.

Further, restriction of the pH low insertion peptide is the same as above.

Further, restriction of the autoimmune diseases is the same as above.

Further, the marker system includes the above marker system.

The sequences in the present invention are sequentially listed from the N terminal to the C terminal.

In the present invention, the "PDL1" and the "PD-L1" may be interchanged.

The present invention has advantages and beneficial effects as follows:

At present, most of the clinical and preclinical researches of the autoimmune diseases are to block functions of a certain cytokine (IL-6/TNF-α/IL-17) by utilizing an antibody or an antagonist to achieve an aim of alleviating the diseases. However, occurrence of the autoimmune diseases is the result of synergism of multiple factors. In the present application, the PD-1/PD-L1 negative signal of the focus tissue is enhanced by utilizing the pHLIP; and immune response of the effector T cells is suppressed at the source, thereby being expected to achieve a certain curative effect on treatment of the autoimmune diseases.

In the present application, the PD-L1 is accurately shown at the lesion site by utilizing the pHLIP; and the peptide has the characteristic of shorter half-life period, so that potential risk of long-term suppression to the body may be avoided.

DETAILED DESCRIPTION OF THE INVENTION

Figure 1:
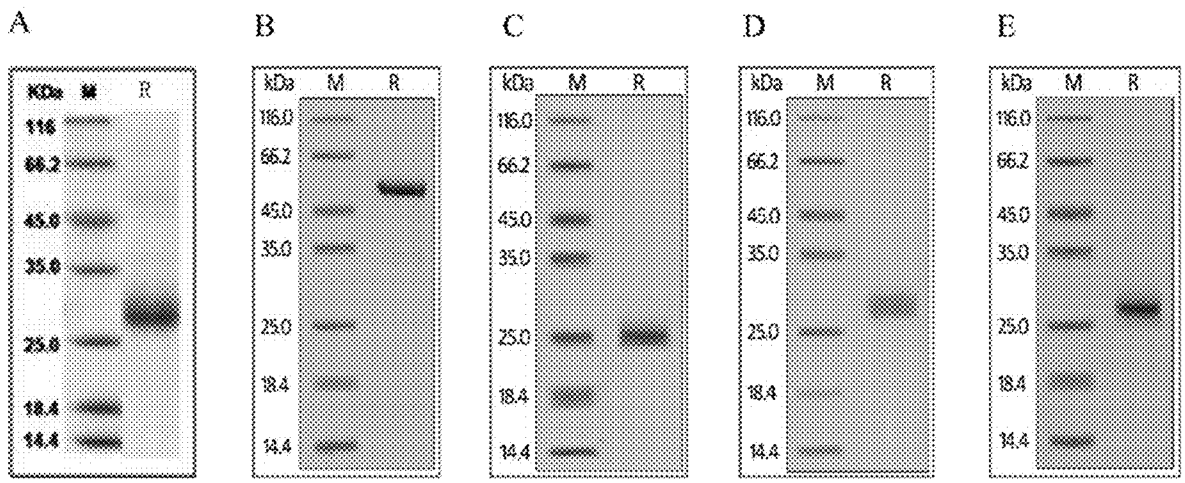
FIG. 1 shows an SDS-PAGE chromosome map of a synthetic peptide in the present invention, wherein A: PD-L1-WTpHLIP; B: PDL1-Ig; C: extracellular domain of PD-L1; D: PDL1-var3; E: PD-L1-var7.

The following embodiments are included to illustrate preferred implementation modes of the present invention. Those skilled in the art should understand that, technologies disclosed in embodiments below represent technologies that are discovered by the inventor and that achieve excellent functions in practice of the present invention. Therefore, the embodiments below are considered as preferred implementation modes forming the practice of the present invention. However, according to the present disclosure, those skilled in the art should understand that, multiple changes may be conducted in specific implementation modes, and identical or similar results are still obtained without departing from the aim and scope of the present invention. The present invention is not limited to the scope of the specific implementation modes in the present invention. The implementation modes mean individual examples of various aspects in the present invention; and functionally identical methods and components also fall within the scope of the present invention. In fact, in addition to the changes in the present invention, multiple changes of the present invention are obvious to those skilled in the art due to the above description. These changes will fall within the scope of claims.

Embodiment 1 Peptide Synthesis

Wild-type pHLIP (having an amino acid sequence shown as SEQ ID NO: 1) and variants 3 and 7 thereof are respectively expressed as WTpHLIP, var3 and var7, and are all synthesized by Chinese Peptide Company.

An extracellular domain of PDL1 (having an amino acid sequence shown as SEQ ID NO: 18 and a nucleotide sequence shown as SEQ ID NO: 26), fusion peptides that are prepared from the extracellular domain of PD-L1 and wild types pHLIP, var3 and var7 and that are respectively expressed as PDL1-WTpHLIP (having an amino acid sequence shown as SEQ ID NO: 20 and a nucleotide sequence shown as SEQ ID NO: 23), PDL1-var3 (having an amino acid sequence shown as SEQ ID NO: 21 and a nucleotide sequence shown as SEQ ID NO: 24) and PDL1-var7 (having an amino acid sequence shown as SEQ ID NO: 22 and a nucleotide sequence shown as SEQ ID NO: 25), and PDL1-Ig (having an amino acid sequence shown as SEQ ID NO: 27 and a nucleotide sequence shown as SEQ ID NO: 28) are synthesized by the company.

1. Expression Design

According to an *Escherichia coli* expression design gene sequence, a restriction site Nde I was used at a terminal 5', and a restriction site XhoI for a terminator was added at a terminal 3'.

2. Strain Construction

A vector PET28a was respectively constructed by utilizing the restriction sites Nde I and XhoI; receptor bacteria BL21 (DE3) were transformed after construction; and clone was picked for validation (sequencing and expression).

3. Culture and Induction

The strain that was validated accurate was cultured (by an LB medium) and then induced (IPTG0.5 mM) when a value OD was up to 0.6-0.8; and then the strain was centrifuged for 4-6 hours for recovery.

4. Extraction and Purification (1) Inclusion body washing

Solution A: 50 mM Tris and 2 mM EDTA, pH of 8.0, washed twice;

Solution B: 50 mM Tris, 2 mM EDTA and 0.1% Triton, pH of 8.0, washed once;

Solution C: 20 mM Tris and 1M urea, pH of 8.0, washed once.

(2) Extraction: the inclusion body was extracted with 8M urea, 5 mM β-Me, 0.3M NaCl and 20 mM Tris at a pH of 8.0, wherein an extraction ratio was 1:20.

(3) Renaturation dialysis: 10 mM β-Me was added to a target protein; the protein was reduced at 40° C. for 15 minutes and diluted to 0.2 mg/ml with 10 mM PBS; the sample was dialyzed with 50 μM $CuCl_2$ at a pH of 8.0; dialysate was changed for 3 times; and then the supernatant was collected after centrifugation.

(4) Ni column purification: a chromatographic column was balanced with 0.3M NaCl and 10 mM PBS at a pH of 8.0; impurities were washed with equilibration buffer containing 40 mM imidazole after loading; and the target protein was eluted with equilibration buffer containing 300 mM imidazole. Purity of the target protein was higher than 95%.

(5) The protein was desalinized in 20 mM PBS and 0.1M NaCl.

5. Coomassie Blue Staining Results

The purified peptide was subjected to SDS-PAGE. Coomassie blue staining results were shown as FIG. 1, which indicated that peptide expression was successful.

Embodiment 2 Study of Ability of PDL1-WT pHLIP Binding Ligand

I. ELISA Experiment of Binding of PD-1 and PDL1-WT pHLIP

1. Experimental Materials

Reagents: biotin (BioLegend), PDL1-WT pHLIP and PBS (Gibco).

2. Instruments

Microplate washer and microplate reader

3. Experimental Grouping

PDL1-WT pHLIP group; WTpHLIP control group; BSA control group and BLANK group

4. Experimental Method (1) The PDL1-WT pHLIP, WT pHLIP and BSA were subjected to gradient envelope at an initial concentration of 50 μg/ml, and stayed overnight at 4° C.

(2) The microplate was washed by the microplate washer for 3 times; and casein sealing was conducted at 37° C. for 1 h.

(3) biotin-PD-1 (1 μg/ml) was added at 37° C. for 1 h.

(4) A second antibody was added for keeping in dark place at a room temperature for 45 min.

(5) A developing solution was added for developing for 5 min.

(6) Sulfuric acid termination was conducted, and reading was conducted by the microplate reader at 450 nm.

II. ELISA Experiment of Binding of PD-1 and Extracellular Domain of PDL1

1. Experimental Materials

Reagents: biotin (BioLegend), extracellular domain of PD-L1 and PBS (Gibco).

2. Instruments

Microplate washer and microplate reader

3. Experimental Grouping

PDL1 extracellular domain group, PDL1-WT pHLIP group; WTpHLIP control group; BSA control group and BLANK group 4. Experimental Method (1) The PDL1 extracellular domain, PDL1-WT pHLIP, WT pHLIP and BSA were subjected to gradient envelope at an initial concentration of 50 μg/ml, and stayed overnight at 4° C.

(2) The microplate was washed by the microplate washer for 3 times; and casein sealing was conducted at 37° C. for 1 h.

(3) biotin-PD-1 (1 μg/ml) was added at 37° C. for 1 h.

(4) A second antibody was added for keeping in dark place at a room temperature for 45 min.

(5) A developing solution was added for developing for 5 min.

(6) Sulfuric acid termination was conducted, and reading was conducted by the microplate reader at 450 nm.

III. Experiment of Binding of Biotin-PDL1 Antibody and PDL1-WT pHLIP

1. Experimental Materials

Reagents: biotin-anti-PDL1 (BioLegend), PDL1-WT pHLIP and PBS (Gibco).

2. Instruments

Microplate washer and microplate reader

3. Experimental Grouping

PDL1-WT pHLIP group; WTpHLIP control group; BSA control group and BLANK group

4. Experimental Method (1) The PDL1-WT pHLIP, WT pHLIP and BSA were subjected to gradient envelope at an initial concentration of 50 μg/ml, and stayed overnight at 4° C.

(2) The microplate was washed by the microplate washer for 3 times; and casein sealing was conducted at 37° C. for 1 h.

(3) biotin-anti-PDL1 (1 μg/ml) was added at 37° C. for 1 h.

(4) A second antibody was added for keeping in dark place at a room temperature for 45 min.

(5) A developing solution was added for developing for 5 min.

(6) Sulfuric acid termination was conducted, and reading was conducted by the microplate reader at 450 nm.

IV. Results

Figure 2:
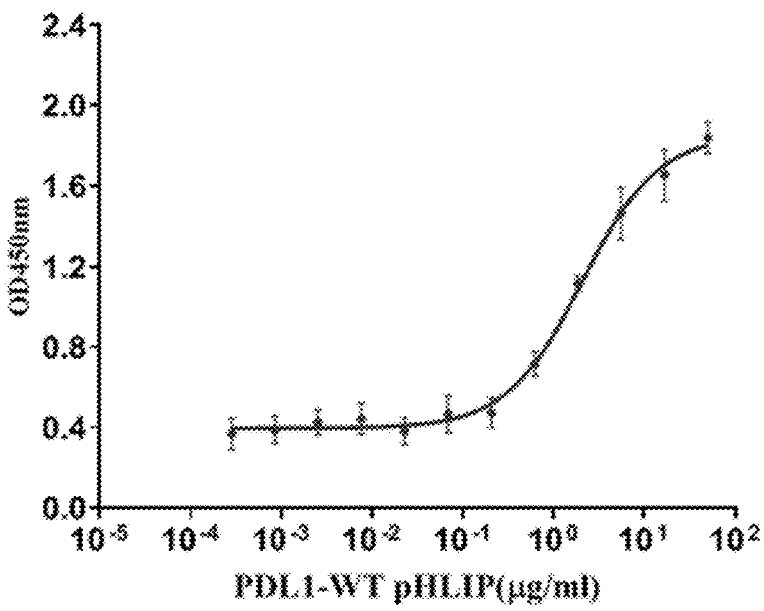
FIG. 2 shows an ELISA result map of binding of PDL1-WT pHLIP and PD-1.
Figure 3:
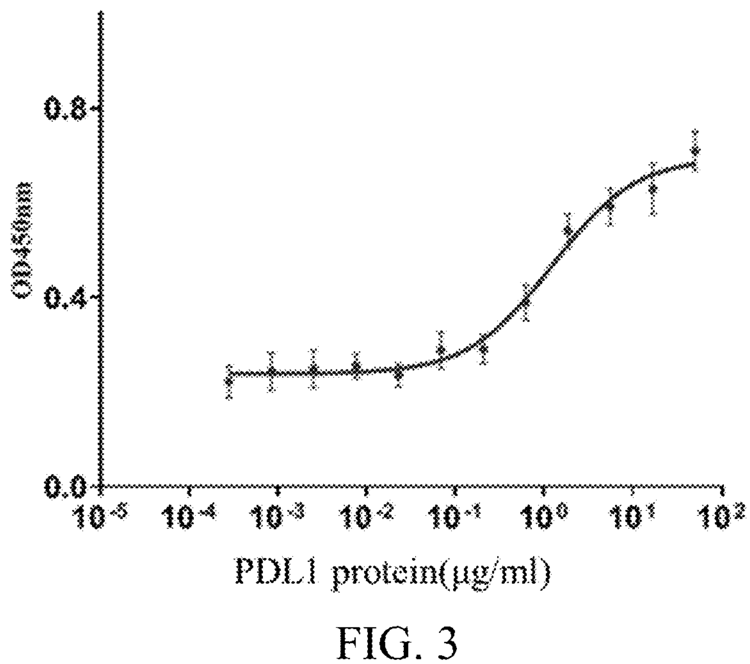
FIG. 3 shows an ELISA result map of binding of PD-1 and a PDL1 protein.
Figure 4:
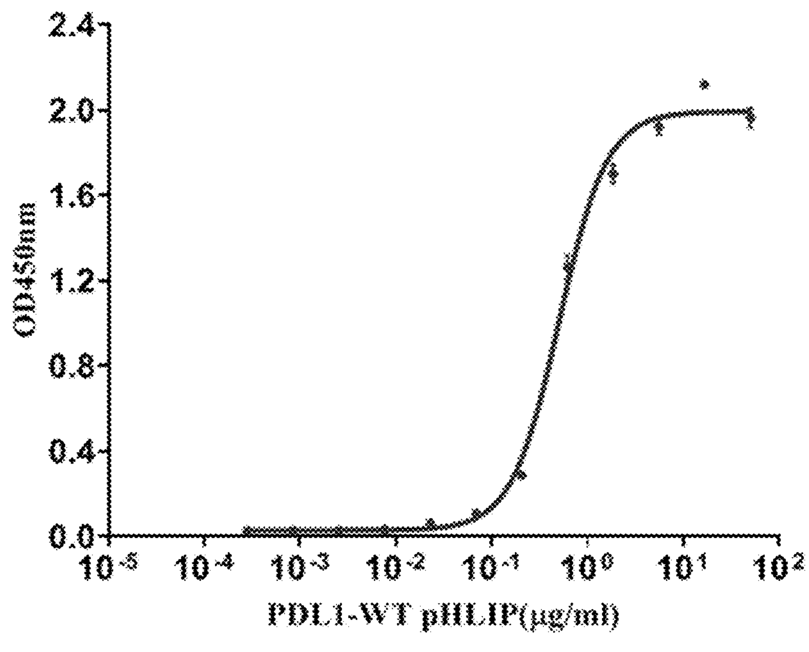
FIG. 4 shows an ELISA result map of binding of PDL1-WT pHLIP and a PDL1 antibody.

The results were shown as FIGS. 2-4. The EC50 was equal to 2.058 μg/ml during binding of the PDL1-WT pHLIP and the PD-1; the EC50 was equal to 1.213 μg/ml during binding of the PD-1 and the extracellular domain of PDL1; and the EC50 was equal to 0.5066 μg/ml during binding of the PDL1-WT pHLIP and the PDL1 antibody. The above results showed that, the binding ability of the PDL1-WT pHLIP and the PD-1 was equivalent to the extracellular domain of PDL1; and the binding of the PDL1 and PD-1 was not affected by linking of the pHLIP.

Embodiment 3 Study of Ability of PDL1-var3 Binding Ligand

I. ELISA Experiment of Binding of PD-1 and PDL1-var3

1. Experimental Materials

Reagents: biotin (BioLegend), PDL1-var3 and PBS (Gibco).

2. Instruments

Microplate washer and microplate reader

3. Experimental Grouping

PDL1-var3 group; var3 control group; BSA control group and BLANK group

4. Experimental Method (1) The PDL1-var3, var3 and BSA were subjected to gradient envelope at an initial concentration of 50 μg/ml, and stayed overnight at 4° C.

(2) The microplate was washed by the microplate washer for 3 times; and casein sealing was conducted at 37° C. for 1 h.

(3) biotin-PD-1 (1 μg/ml) was added at 37° C. for 1 h.

(4) A second antibody was added for keeping in dark place at a room temperature for 45 min.

(5) A developing solution was added for developing for 5 min.

(6) Sulfuric acid termination was conducted, and reading was conducted by the microplate reader at 450 nm.

II. Experiment of Binding of Biotin-PDL1 and PDL1-var3

1. Experimental Materials

Reagents: biotin-anti-PDL1 (BioLegend), PDL1-var3 and PBS (Gibco).

2. Instruments

Microplate washer and microplate reader

3. Experimental Grouping

PDL1-var3 group; var3 control group; BSA control group and BLANK group

4. Experimental Method (1) The PDL1-var3, var3 and BSA were subjected to gradient envelope at an initial concentration of 50 μg/ml, and stayed overnight at 4° C.

(2) The microplate was washed by the microplate washer for 3 times; and casein sealing was conducted at 37° C. for 1 h.

(3) biotin-anti-PDL1 (1 μg/ml) was added at 37° C. for 1 h.

(4) A second antibody was added for keeping in dark place at a room temperature for 45 min.

(5) A developing solution was added for developing for 5 min.

(6) Sulfuric acid termination was conducted, and reading was conducted by the microplate reader at 450 nm.

IV. Results

Figure 5:
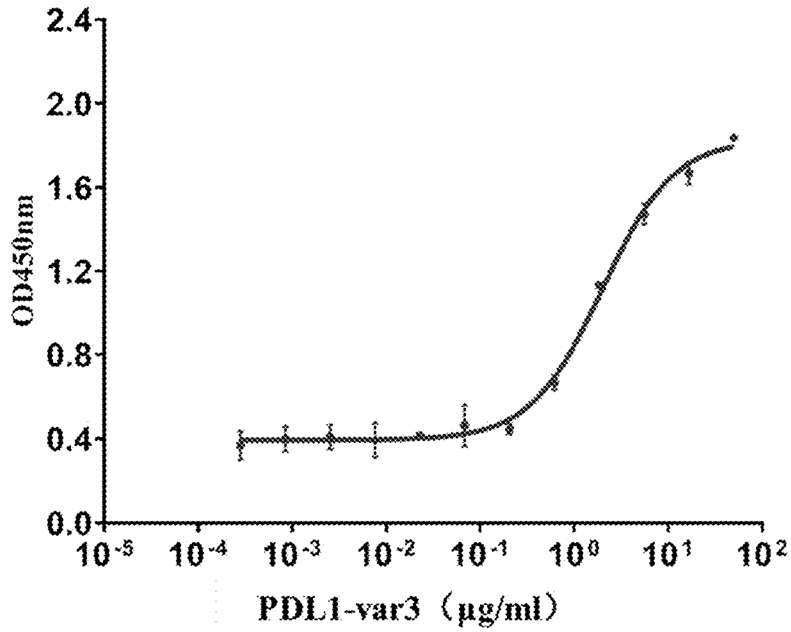
FIG. 5 shows an ELISA result map of binding of PDL1-var3 and PD-1.
Figure 6:
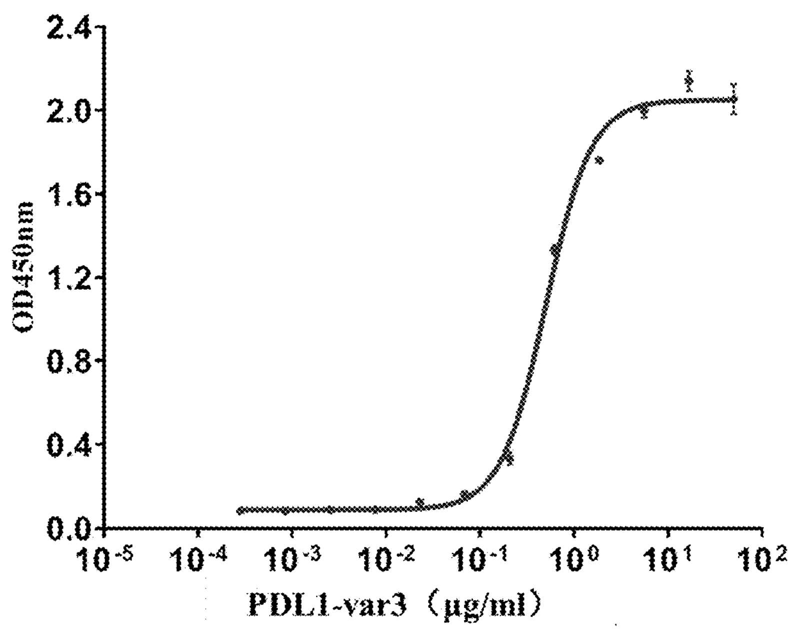
FIG. 6 shows an ELISA result map of binding of PDL1-var3 and a PDL1 antibody.

The results were shown as FIGS. 5 and 6. The EC50 was equal to 1.985 μg/ml during binding of the PDL1-var3 and the PD-1; and the EC50 was equal to 0.5018 μg/ml during binding of the PDL1-var3 and the PDL1. The above results showed that, the binding ability of the PDL1-var3 and the PD-1 was equivalent to the extracellular domain of PDL1; and the binding of the PDL1 and PD-1 was not affected by linking of the var3.

Embodiment 4 Study of Ability of PDL1-var7 Binding Ligand

I. ELISA Experiment of Binding of PD-1 and PDL1-var7

1. Experimental Materials

Reagents: biotin (BioLegend), PDL1-var7 and PBS (Gibco).

2. Instruments

Microplate washer and microplate reader

3. Experimental Grouping

PDL1-var7 group; var7 control group; BSA control group and BLANK group

4. Experimental Method (1) The PDL1-var7, var7 and BSA were subjected to gradient envelope at an initial concentration of 50 μg/ml, and stayed overnight at 4° C.

(2) The microplate was washed by the microplate washer for 3 times; and casein sealing was conducted at 37° C. for 1 h.

(3) biotin-PD-1 (1 μg/ml) was added at 37° C. for 1 h.

(4) A second antibody was added for keeping in dark place at a room temperature for 45 min.

(5) A developing solution was added for developing for 5 min.

(6) Sulfuric acid termination was conducted, and reading was conducted by the microplate reader at 450 nm.

II. Experiment of Binding of Biotin-PDL1 and PDL1-var7

1. Experimental Materials

Reagents: biotin-anti-PDL1 (BioLegend), PDL1-var7 and PBS (Gibco).

2. Instruments

Microplate washer and microplate reader

3. Experimental Grouping

PDL1-var7 group; var7 control group; BSA control group and BLANK group

4. Experimental Method (1) The PDL1-var7, var7 and BSA were subjected to gradient envelope at an initial concentration of 50 μg/ml, and stayed overnight at 4° C.

(2) The microplate was washed by the microplate washer for 3 times; and casein sealing was conducted at 37° C. for 1 h.

(3) biotin-anti-PDL1 (1 μg/ml) was added at 37° C. for 1 h.

(4) A second antibody was added for keeping in dark place at a room temperature for 45 min.

(5) A developing solution was added for developing for 5 min.

(6) Sulfuric acid termination was conducted, and reading was conducted by the microplate reader at 450 nm.

IV. Results

Figure 7:
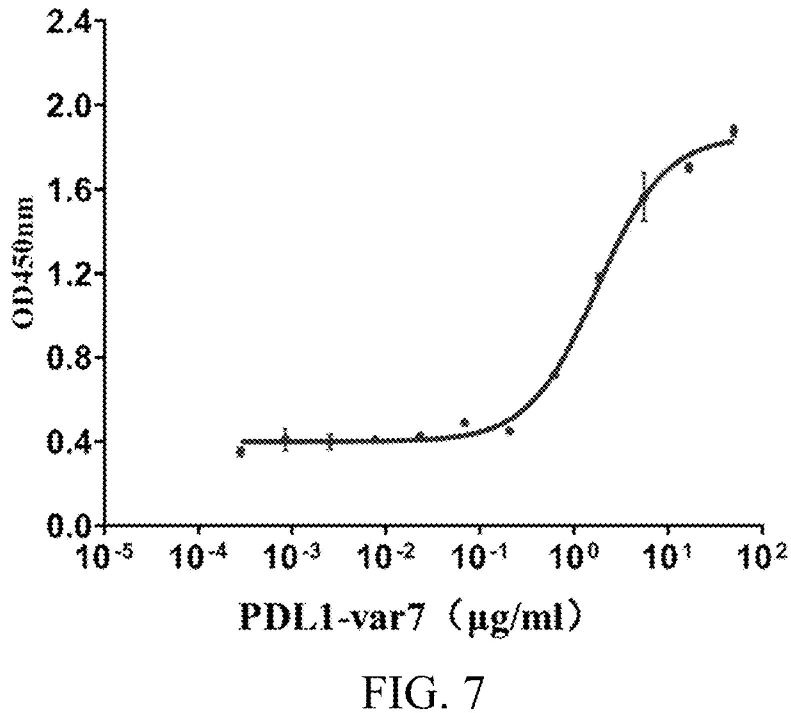
FIG. 7 shows an ELISA result map of binding of PDL1-var7 and PD-1.
Figure 8:
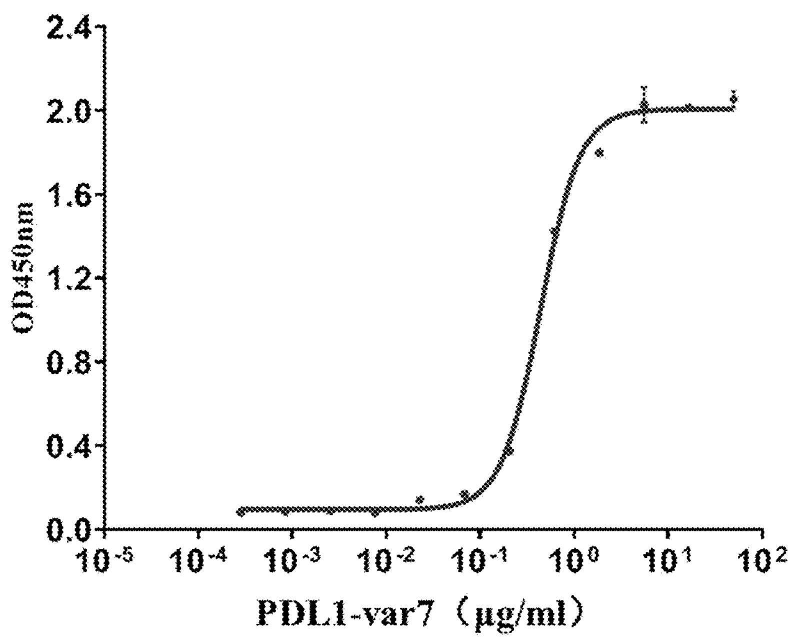
FIG. 8 shows an ELISA result map of binding of PDL1-var7 and a PDL1 antibody.

The results were shown as FIGS. 7 and 8. The EC50 was equal to 1.743 μg/ml during binding of the PDL1-var7 and the PD-1; and the EC50 was equal to 0.4406 μg/ml during binding of the PDL1-var7 and the PDL1. The above results showed that, the binding ability of the PDL1-var7 and the PD-1 was equivalent to the extracellular domain of PDL1; and the binding of the PDL1 and PD-1 was not affected by linking of the var7.

Embodiment 5 Localization of Fusion Peptide on Cells

1. Cell Line

Human embryonic kidney cell line HEK293 (purchased from ATCC).

2. Reagents DMEM medium (Gibco), fetal calf serum (Gibco), PBS (pH=7.4) (Gibco), Tris-HCL (1 mol/mL), PD-1, PDL1 extracellular domain, PDL1-WT pHLIP, PDL1-WT pHLIP, PDL1-var7, var7, PDL1-var3, var7 and PE crosslinking kits (Expedeon Company).

3. Instruments

Super clean bench; carbon dioxide incubator (Thermo); centrifuge (Thermo); laser confocal cell-culture dish (Corning); electronic pH indicator (Sartorius); optical microscope (Nikon); laser scanning confocal microscope (Zeiss LSM 880).

4. Experimental Steps

HEK293 cells in a logarithmic phase were collected; a culture solution was removed; and the cells were washed with PBS twice. An appropriate amount of pancreatin was added for digestion; digestion was terminated with the culture solution; the solution was transferred into a 10 ml test tube; the solution was centrifuged at 1000 rpm for 5 min; the supernatant was removed; and 1 mL of DMEM medium containing 10% of fetal calf serum was added for resuspending and uniform mixing. 10 μL of cell suspension was sucked into a cell counting plate for counting; a certain amount of cell suspension was added into the laser confocal cell-culture dish and adjusted to $5*10^5$ with a medium; and 1 mL of cell system was cultured in the incubator overnight.

After attachment of the cultured HEK293 cells, the supernatant was removed; and the solution was washed twice with PBS buffer having a pH value of 7.4.

A culture solution was prepared from 1 mol/mL of hydrochloric acid and the PBS buffer having the pH value of 7.4; the hydrochloric acid was added into the PBS dropwise; and finally the pH value of the buffer was titrated to 6.3 (5 mL of PBS buffer+12 μL of Tris-hydrochloric acid). PDL1-WT pHLIP, or PDL1-var3 or PDL1-var7 was respectively added into PBS buffer having pH values of 7.4 and 6.3 to be fully and uniformly mixed; and the peptide was diluted to a final concentration of 200 μg/mL according to a ratio. In a control group, a PDL1 extracellular domain having a final concentration of 180 μg/mL and WT pHLIP or var3 or var7 having a final concentration of 20 μg/mL were added into the PBS buffer having pH values of 7.4 and 6.3.

The PBS buffer in the culture dish was removed; 1 mL of the above mixed solution was respectively added; 1 mL of unmixed PBS buffer having respective pH values of 7.4 and 6.3 was added into a blank control group; and the cells were incubated in a cell incubator at 37° C. for 1 hour.

The supernatant was removed after completion of incubation; the solution was washed twice with the PBS buffer having corresponding pH values; 1 mL of 1 μg/mL PD-1-PE was added; and the cells were incubated in a dark place at 4° C. for half an hour.

The solution was washed twice with the PBS having corresponding pH values after completion of incubation; and then PBS buffer having corresponding pH values was added.

The prepared culture dish was placed under the laser scanning confocal microscope for observing the fluorescence situation on the surface of the cell membrane.

5. Results

Figure 9:
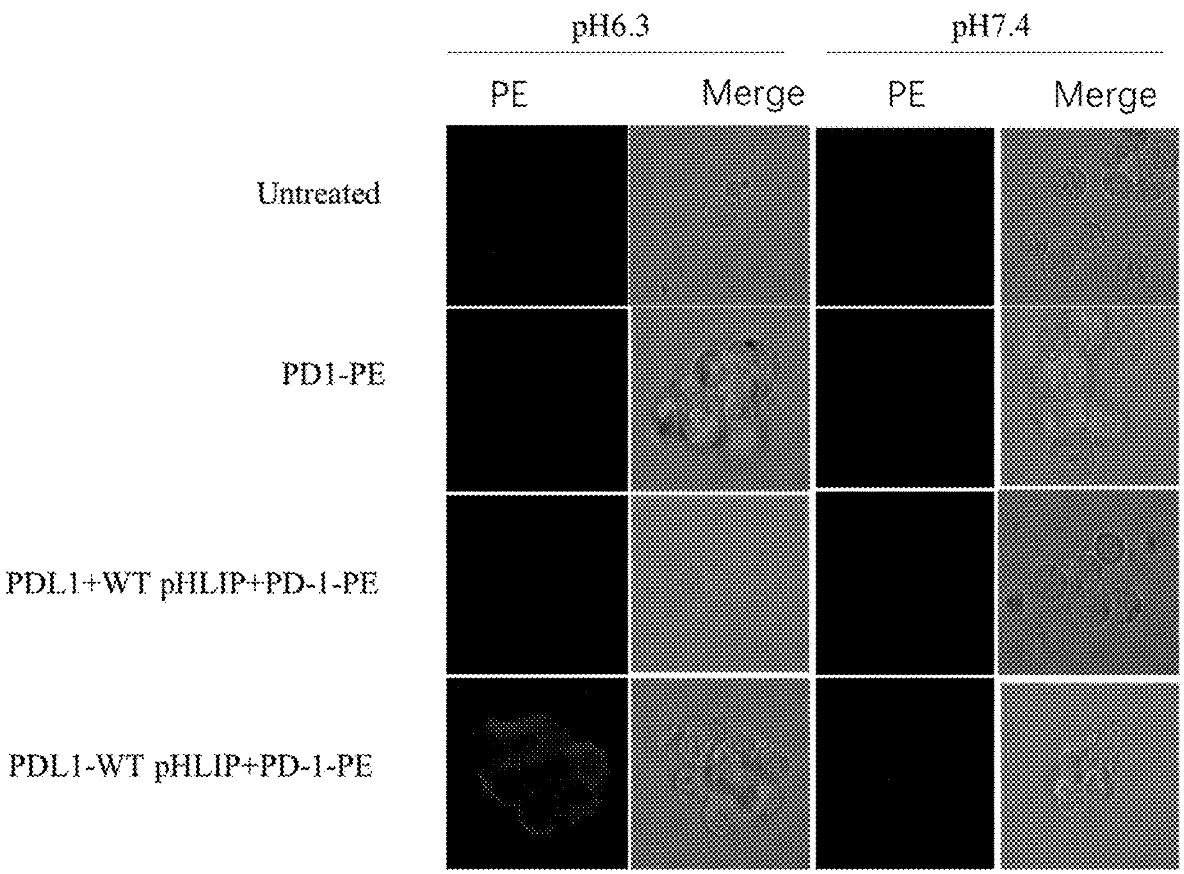
FIG. 9 shows a fluorogram of PDL1-WT pHLIP localization on HEK293 cells observed by utilizing confocal.

The results were shown as FIG. 9. The PDL1-pHLIP can be well shown on the surface of the cell membrane in an acid environment. The above result showed that, the PDL1 did not affect the characteristic that the pH low insertion peptide was inserted into the cell membrane; meanwhile, conformation of the PDL1 was not affected during binding of the PDL1 and the pH low insertion peptide.

Figure 10:
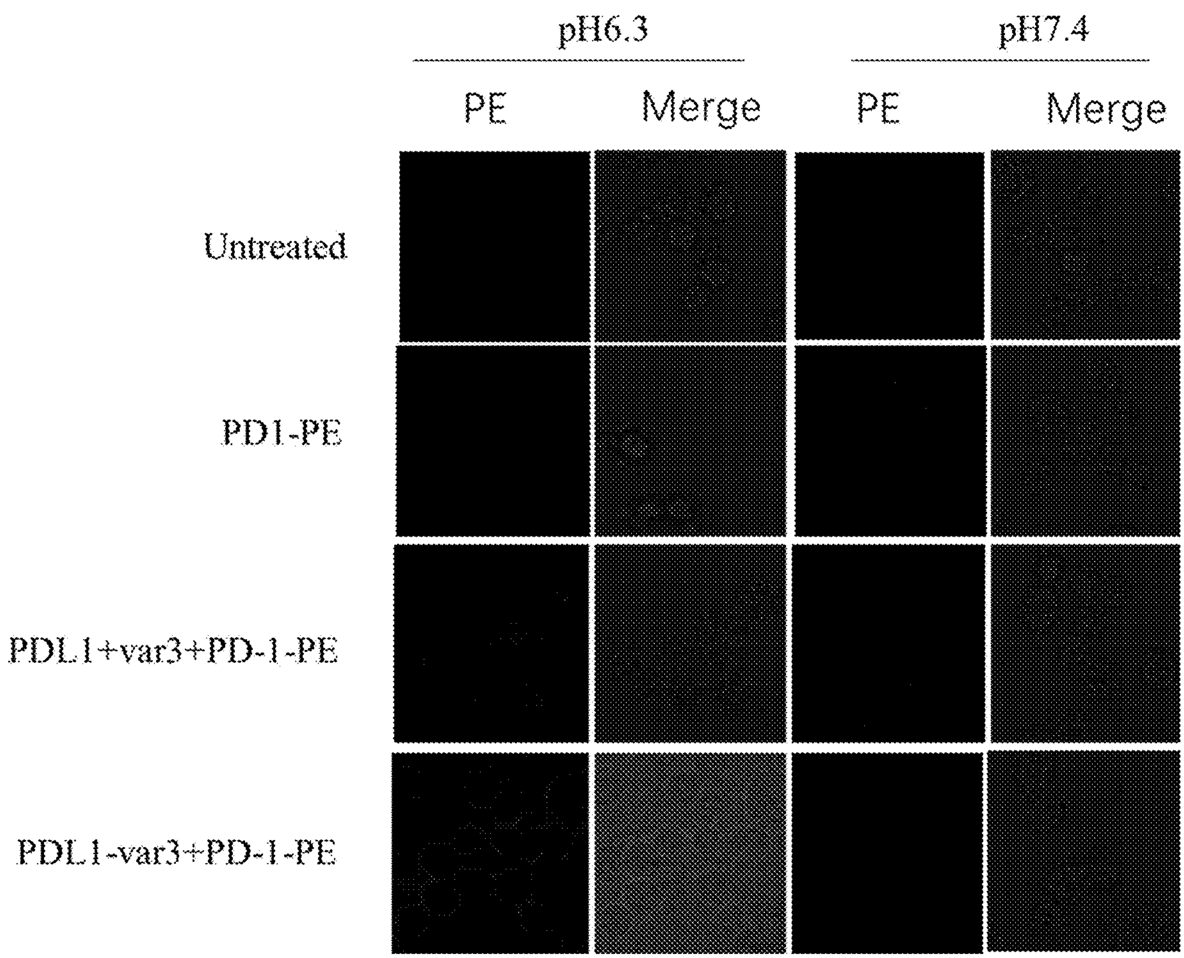
FIG. 10 shows a fluorogram of PDL1-var3 localization on HEK293 cells observed by utilizing confocal.

The results were shown as FIG. 10. The PDL1-var3 can be well shown on the surface of the cell membrane in an acid environment. The above result showed that, the PDL1 did not affect the characteristic that the pH low insertion peptide was inserted into the cell membrane; meanwhile, conformation of the PDL1 was not affected during binding of the PDL1 and the pH low insertion peptide.

Figure 11:
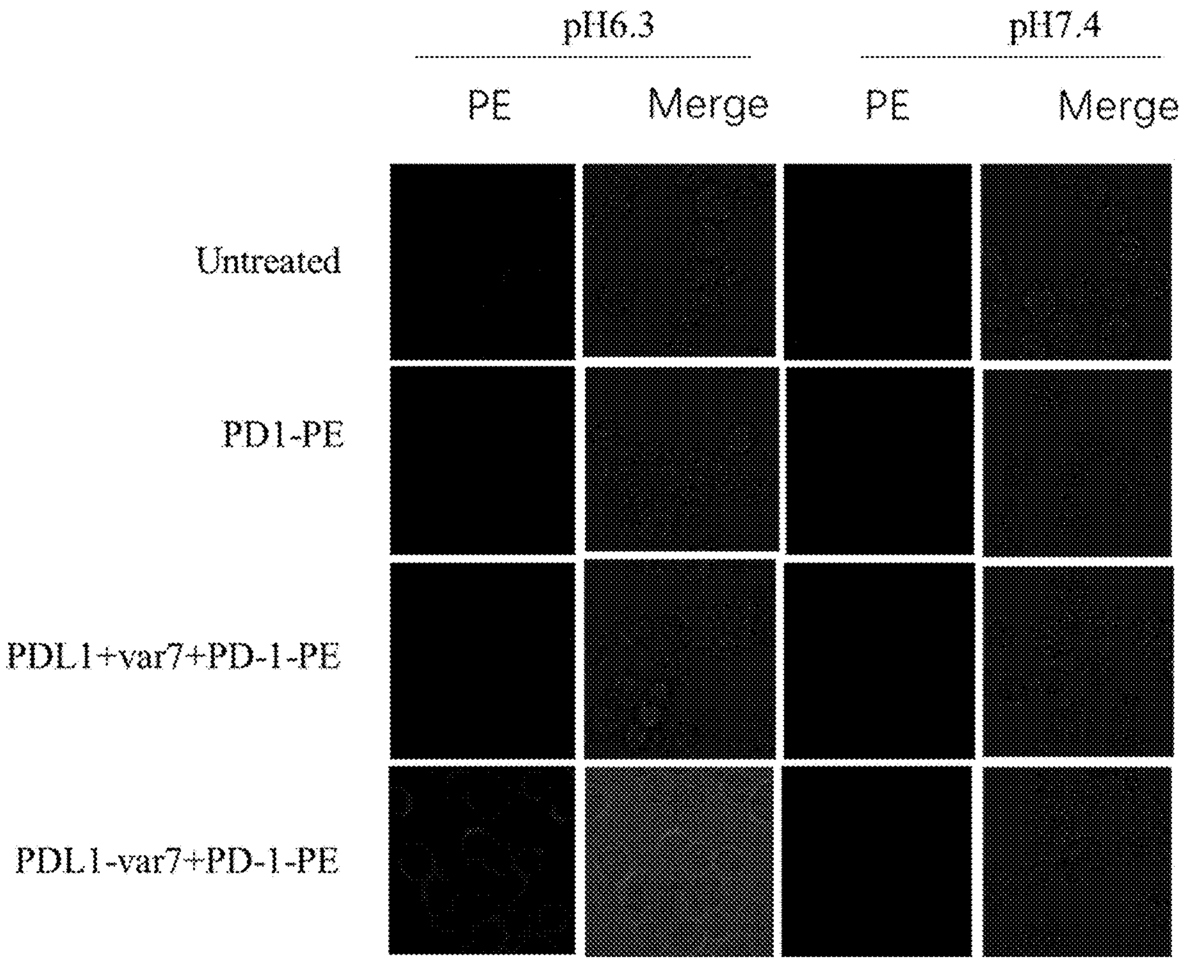
FIG. 11 shows a fluorogram of PDL1-var7 localization on HEK293 cells observed by utilizing confocal.

The results were shown as FIG. 11. The PDL1-var7 can be well shown on the surface of the cell membrane in an acid environment. The above result showed that, the PDL1 did not affect the characteristic that the pH low insertion peptide was inserted into the cell membrane; meanwhile, conformation of the PDL1 was not affected during binding of the PDL1 and the pH low insertion peptide.

Embodiment 6 Effect Evaluation of Fusion Peptide for Treating Autoimmune Diseases 1. Experimental Materials Animal: DBA/1J male mouse (at an age of 7 weeks)

2. Reagents

Chicken collagen II (#20012), complete Freund's adjuvant (#7001) and incomplete Freund's adjuvant (#7002) were all Chondrex, USA; WT pHLIP, var3 and var7 were synthesized by Chinese Peptide Company; and PDL1 extracellular domain, PDL1-WT pHLIP, PDL1-var3, PDL1-var7 and PDL1-Ig were prepared by the company.

3. Instruments

Tissue homogenizer (IKA, H44)

4. Experimental Method

Emulsification of Antigen

Adjuvants of the same volume were added into a 5 ml disposable needle tube; the tissue homogenizer was turned on; a collagen solution was dropped while low-speed stirring; and after the collagens were totally added, the rotation speed was increased until water-in-oil emulsion droplets were formed. The needle tube was placed in an ice bath in the process for preventing protein denaturation.

First immunization: 2 mg/ml of the collagen was mixed with the complete Freund's adjuvant (4 mg/ml) of the same volume; emulsification was conducted (forming a water-in-oil sample); the collagen had a final concentration of 1 mg/ml; and each mouse was injected with 100 μl of the sample, i.e., 100 μg. The needle was inserted from a position that was 2 cm away from the tail head; and injection started when a needle tip position was 0.5 cm away from the tail head.

Second immunization: 2 mg/ml of the collagen was mixed with the incomplete Freund's adjuvant of the same volume; emulsification was conducted; and each mouse was injected with 100 μg of the sample. The injection site was a position that was 3 cm away from the tail head; and a subcutaneous depth of the inserted needle tip was 1.5 cm away from the tail head of the mouse.

Within 2 weeks after the second immunization (then CIA classical symptoms appeared), the experiment was divided into 4 groups: (1) intraperitoneal injection of PDL1-WT pHLIP (or PDL1-var3, or PDL1-var7), 1 mg/kg, administration once every other day; (2) intraperitoneal injection of PDL1 (1 mg/kg)+WT pHLIP (0.2 mg/kg) (or PDL1-var3, or PDL1-var7), administration once every other day; (3) intraperitoneal injection of PDL1-Ig, 1 mg/kg, administration once every other day; and (4) intraperitoneal injection of PBS in the control group. Each group included 10 mice; and heel thicknesses and serum cell factor content were detected within 26 days.

3. Results

Figure 12:
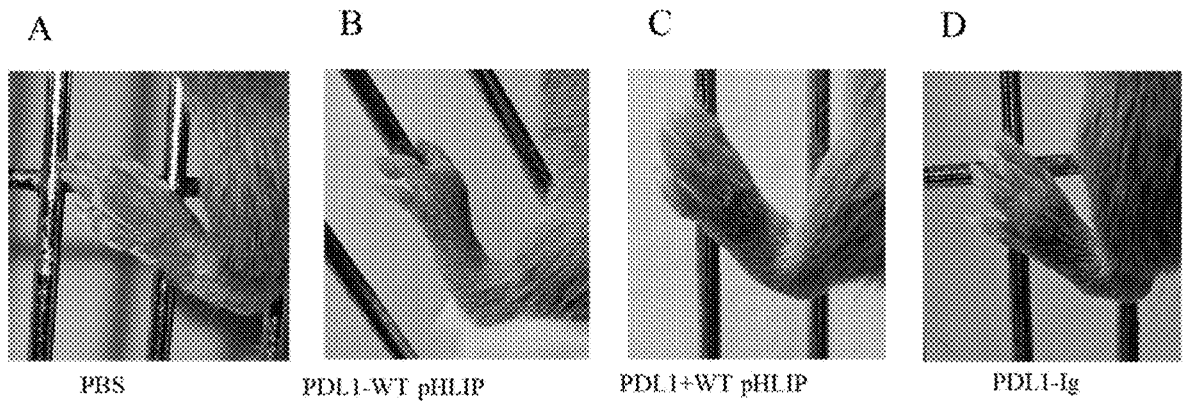
FIG. 12 shows a photo of mouse soles treated with PDL1-WT pHLIP.
Figure 13:
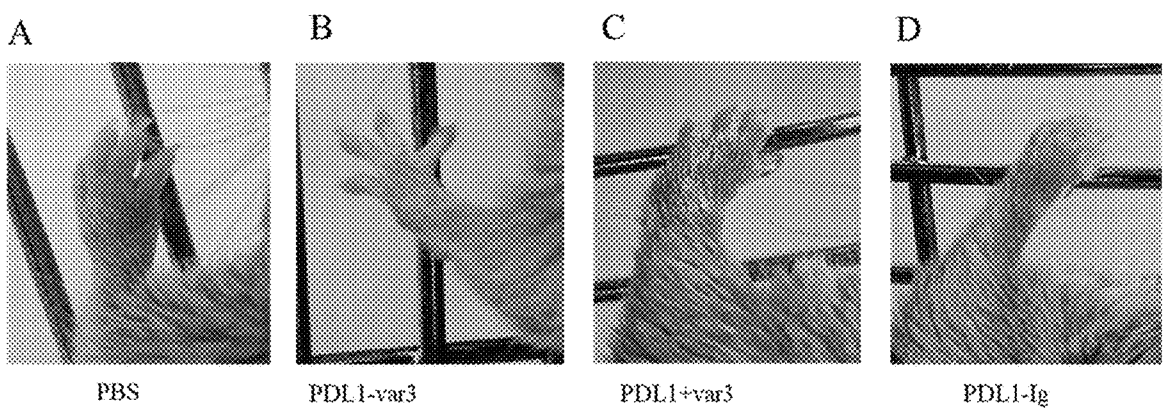
FIG. 13 shows a photo of mouse soles treated with PDL1-var3.
Figure 14:
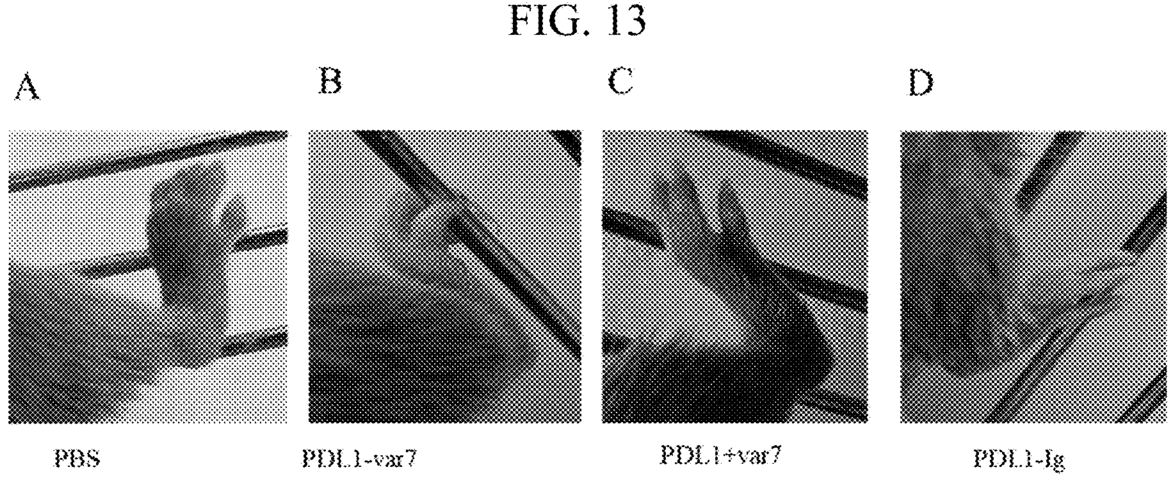
FIG. 14 shows a photo of mouse soles treated with PDL1-var7.
Figure 15:
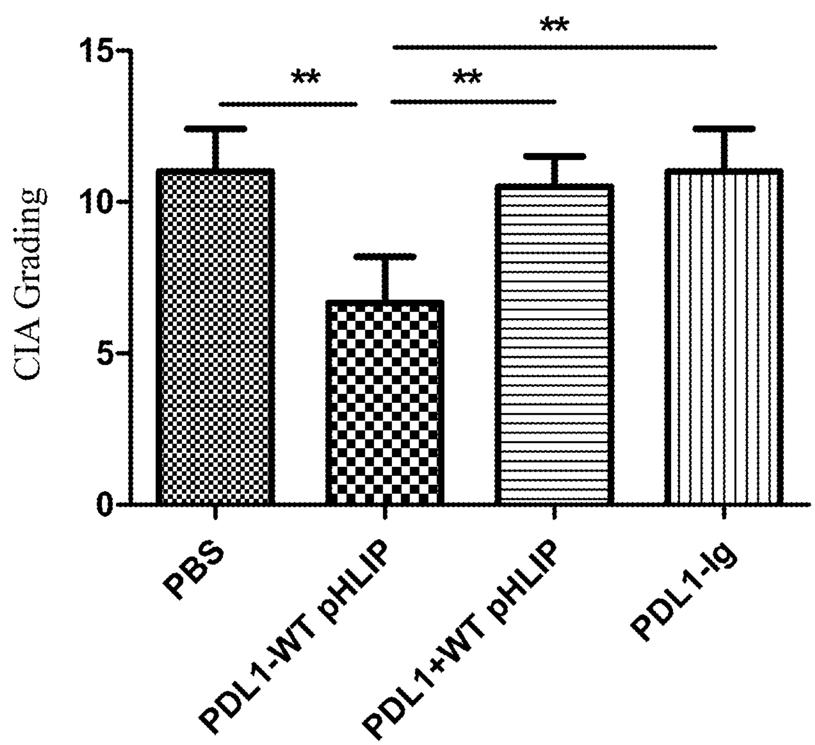
FIG. 15 shows a grading result map of CIA treated with PDL1-WT pHLIP.
Figure 16:
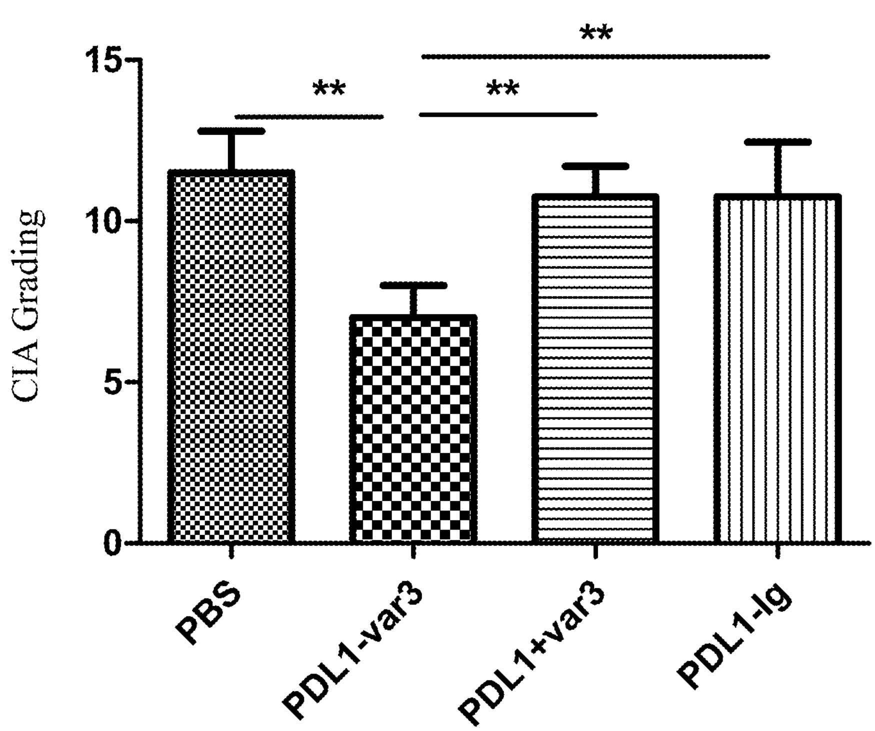
FIG. 16 shows a grading result map of CIA treated with PDL1-var3.
Figure 17:
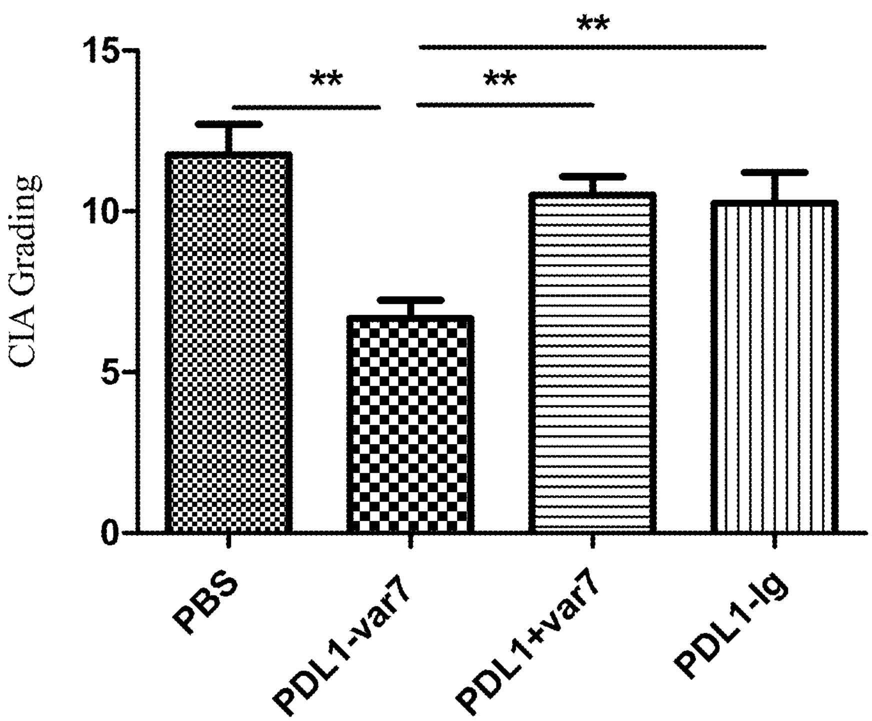
FIG. 17 shows a grading result map of CIA treated with PDL1-var7.

Mouse sole photos in FIGS. 12-14 showed that, the mice in the PDL1-pHLIP group, the PDL1-var3 group or the PDL1-var7 group had normal soles; and inflammation was significantly relieved. CIA grading results were shown as FIGS. 15-17; and CIA grades in the PDL1-pHLIP group, the PDL1-var3 group or the PDL1-var7 group were significantly decreased.

Figure 18:
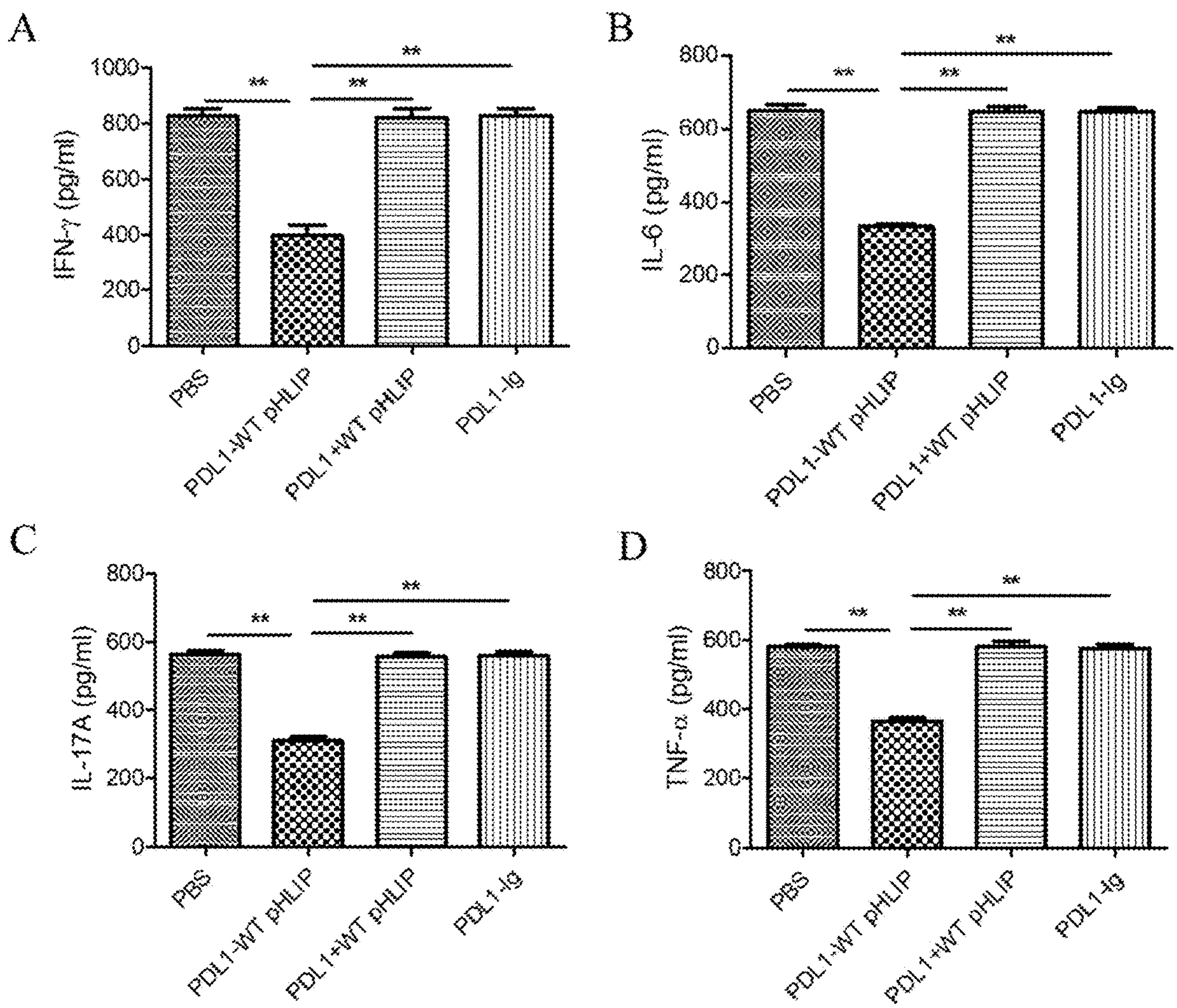
FIG. 18 shows a detection result map of a serum cell factor treated with PDL1-WT pHLIP.
Figure 19:
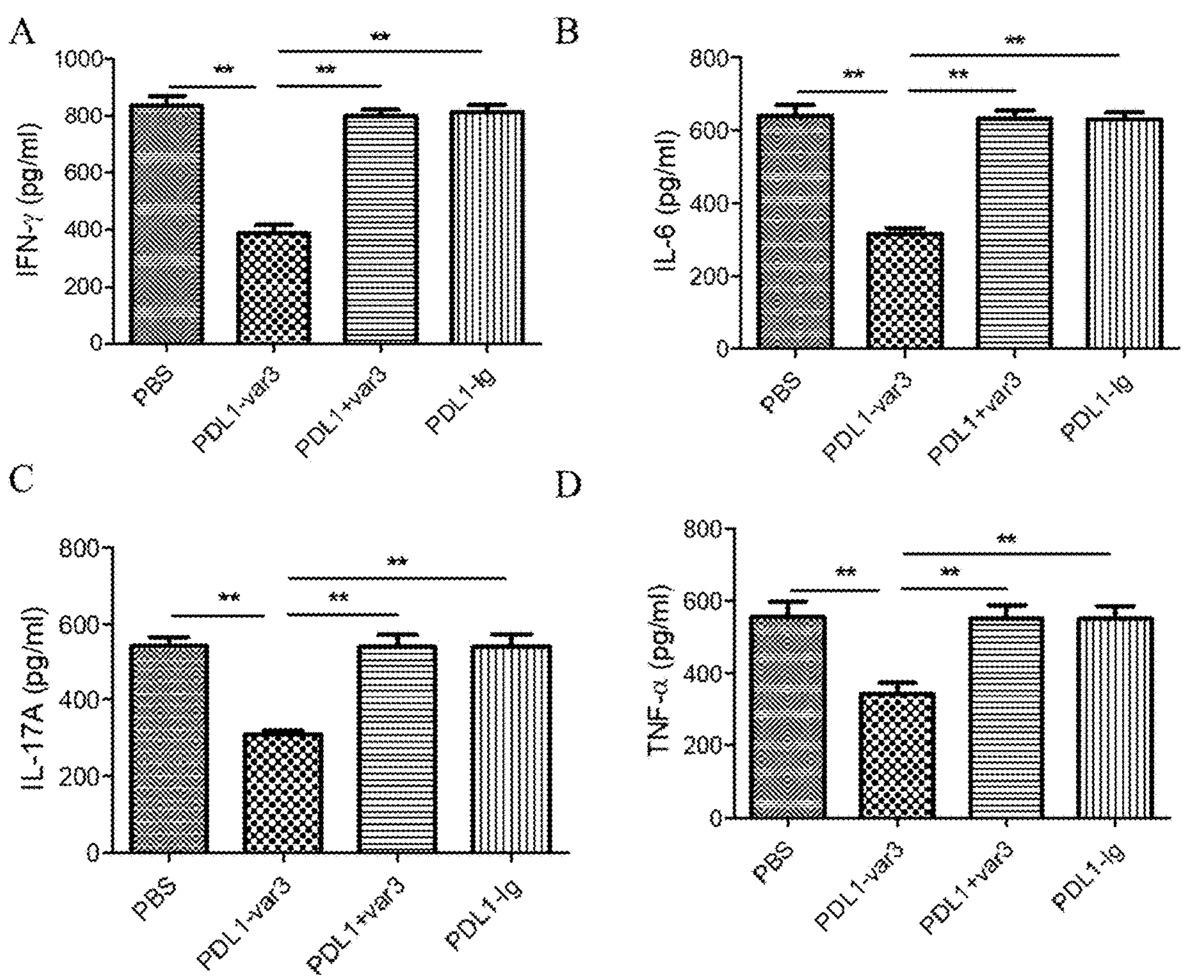
FIG. 19 shows a detection result map of a serum cell factor treated with PDL1-var3.
Figure 20:
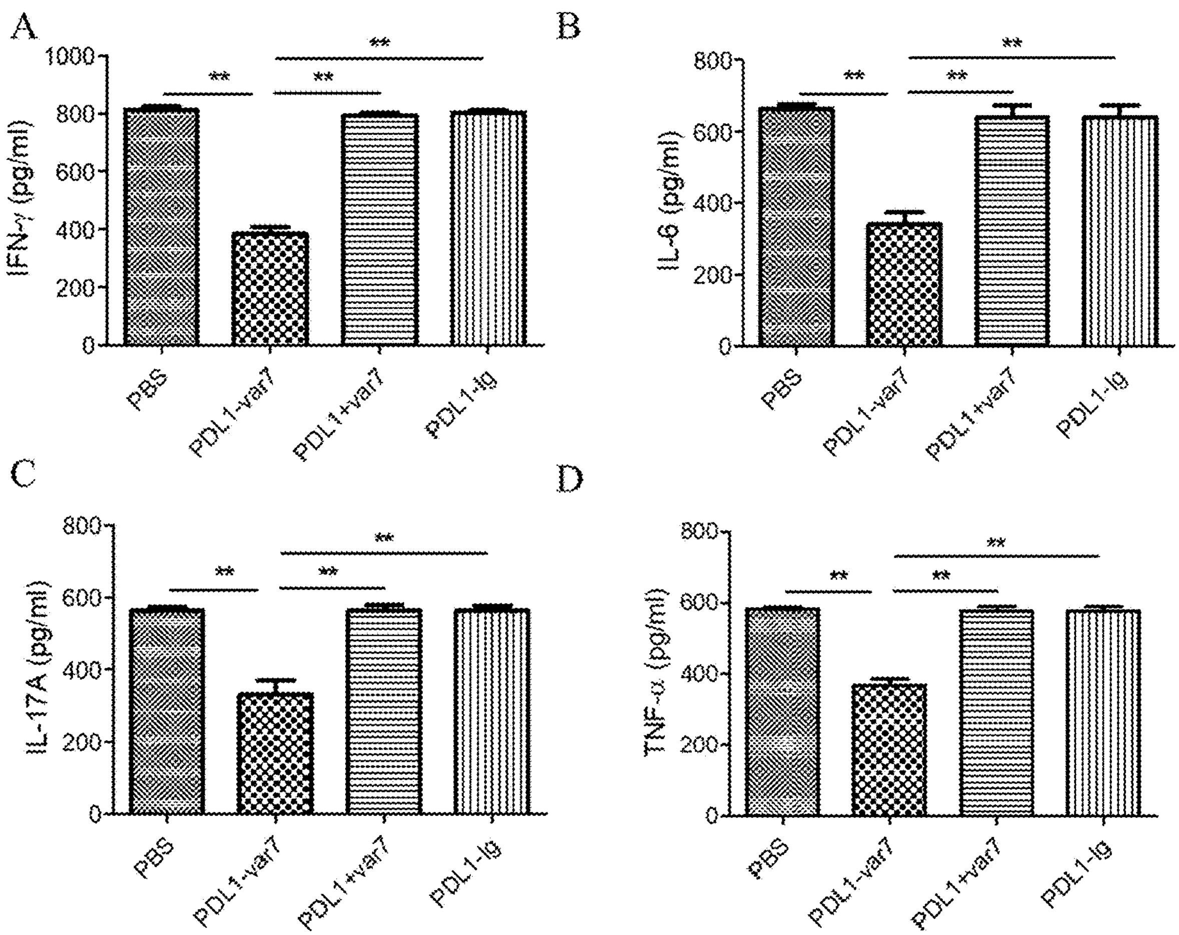
FIG. 20 shows a detection result map of a serum cell factor treated with PDL1-var7.

Serum cell factor detection results were shown as FIGS. 18-20; and content of TNF-α, IFN-γ, IL-6 and IL-17A in the PDL1-pHLIP group, the PDL1-var3 group or the PDL1-var7 group was significantly decreased.

Figure 21:
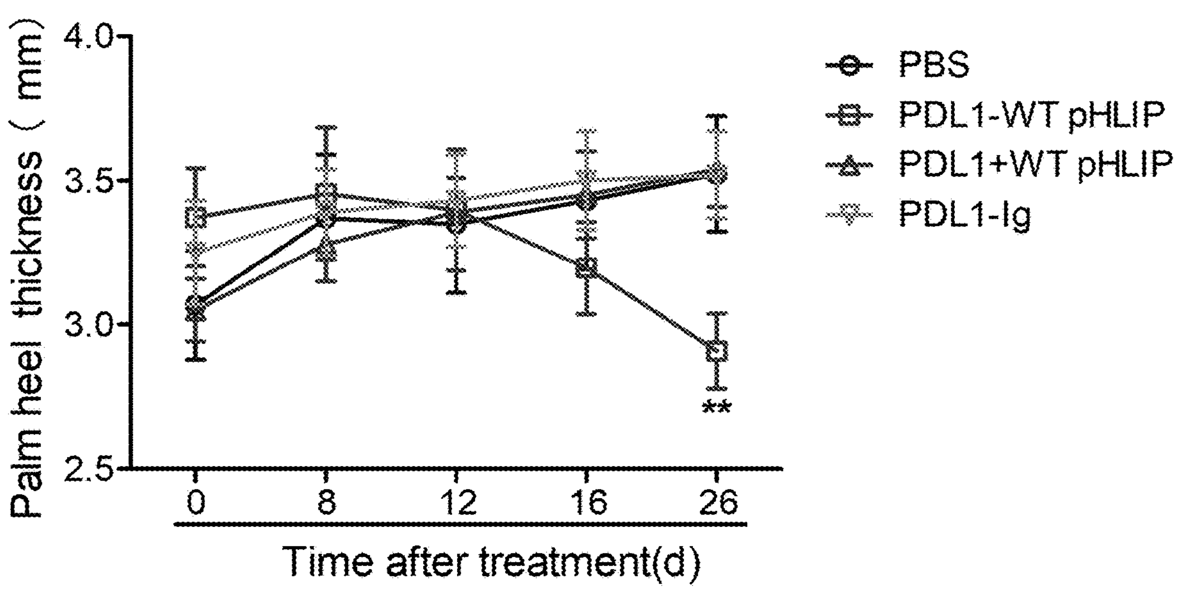
FIG. 21 shows a thickness detection result map of a heel treated with PDL1-WT pHLIP.
Figure 22:
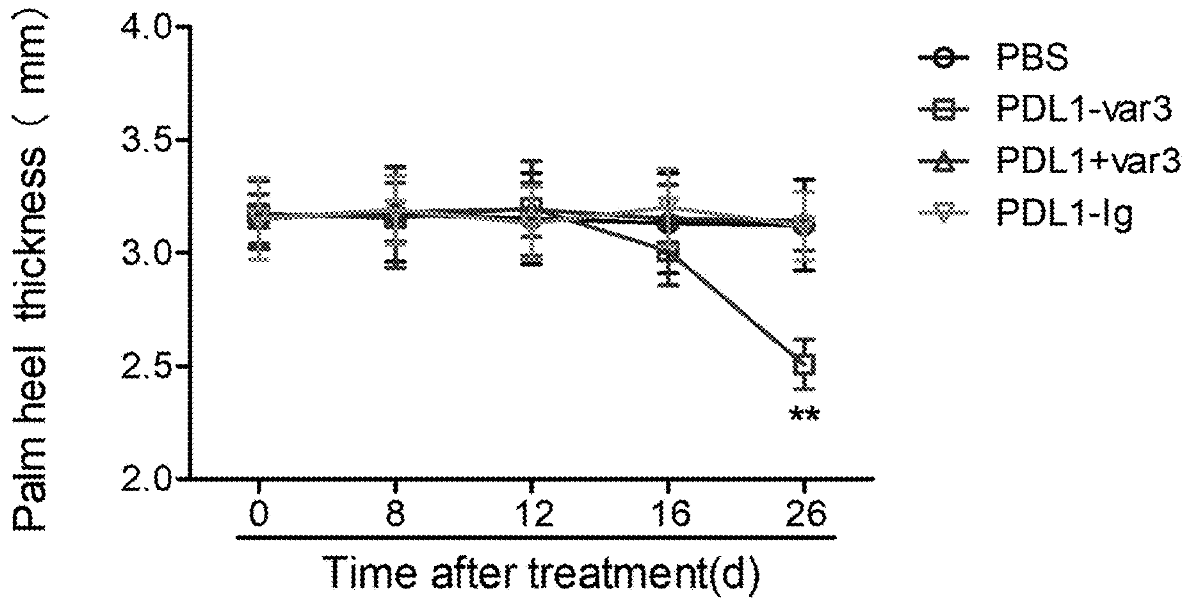
FIG. 22 shows a thickness detection result map of a heel treated with PDL1-var3.
Figure 23:
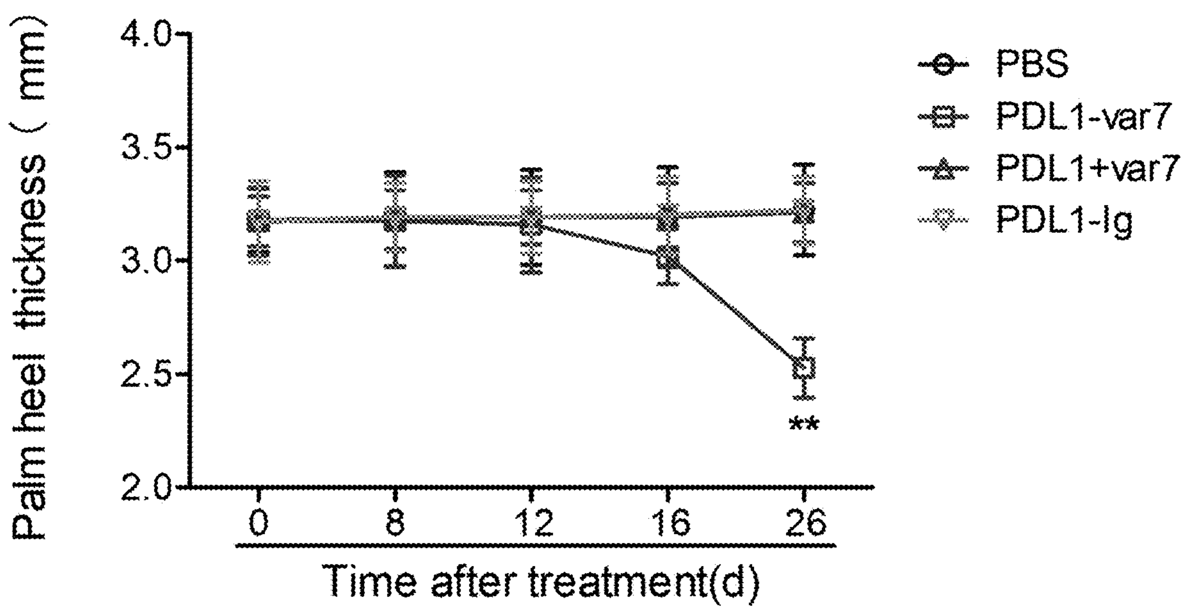
FIG. 23 shows a thickness detection result map of a heel treated with PDL1-var7.

Heel thickness detection results were shown as FIGS. 21-23; and the mouse heel thickness in the PDL1-pHLIP group, the PDL1-var3 group or the PDL1-var7 group was significantly decreased. The above results show that, the fusion peptide in the present invention can significantly alleviate symptoms of the arthritis, which indicates that the fusion peptide has an excellent effect of treating the arthritis.

The invention claimed is:

1. A fusion peptide of a pH low insertion peptide, comprising a pH low insertion peptide and an immune checkpoint ligand, wherein:

the pH low insertion peptide comprises an extracellular domain sequence repeating by one or more times;

the extracellular domain sequence consists of one of the amino acid sequences of SEQ ID NO: 1-17;

the immune checkpoint ligand comprises an extracellular domain of the PD-L1;

the extracellular domain of the PD-L1 comprises the amino acid sequence of SEQ ID NO: 18 or SEQ ID NO: 19; and the extracellular domain of the PD-L1 is bound to an N-terminus of the pH low insertion peptide through a linker.

2. The fusion peptide according to claim 1, wherein the linker comprises the amino acid sequence represented by $(X)_m$, X consists of the sequence of SEQ ID NO: 29 or SEQ ID NO: 30, and m is an integer of 1-10.

3. The fusion peptide according to claim 2, wherein X consists of the sequence of SEQ ID NO: 29.

4. The fusion peptide according to claim 1, wherein the fusion peptide comprises one of the amino acid sequences of SEQ ID NO: 20-22.

5. A pharmaceutical composition, comprising the fusion peptide according to claim 1.

6. A marker system, comprising the fusion peptide according to claim 1.

7. A method for treating rheumatoid arthritis, comprising: administering an effective amount of the fusion peptide according to claim 1 to a patient in need thereof.

8. A method for treating rheumatoid arthritis, comprising: administering an effective amount of the pharmaceutical composition according to claim 5 to a patient in need thereof.

* * * * *